United States Patent
Chiba et al.

(10) Patent No.: US 6,405,578 B2
(45) Date of Patent: Jun. 18, 2002

(54) MAGNETIC OXYGEN ANALYZER

(75) Inventors: Ryuuji Chiba; Hideaki Yamagishi; Masayuki Sato, all of Tokyo (JP)

(73) Assignee: Yokogawa Electric Corporation, Tokyo (JP)

(*) Notice: Subject to any disclaimer, the term of this patent is extended or adjusted under 35 U.S.C. 154(b) by 0 days.

(21) Appl. No.: 09/862,889

(22) Filed: May 22, 2001

(30) Foreign Application Priority Data

May 23, 2000 (JP) .......................... 2000-150754
Apr. 16, 2001 (JP) .......................... 2001-116869

(51) Int. Cl.[7] .......................... G01N 27/74; G01N 29/02
(52) U.S. Cl. .......................... 73/25.02; 73/23.31; 73/25.01; 324/610; 324/706; 324/648; 324/204; 422/98
(58) Field of Search .......................... 73/25.02, 25.03, 73/23.31, 31.05, 25.05, 25.01; 422/98; 324/610, 648, 693, 706, 204

(56) References Cited

U.S. PATENT DOCUMENTS

| | | | | |
|---|---|---|---|---|
| 2,603,965 A | * | 7/1952 | Medlock | 73/27 |
| 2,658,385 A | * | 11/1953 | Richardson | 73/27 |
| 2,693,103 A | * | 11/1954 | Krupp | 73/27 |
| 2,729,097 A | * | 1/1956 | Cherrier | 73/27 |
| 2,815,659 A | * | 12/1957 | Krupp | 73/27 |
| 2,903,883 A | * | 9/1959 | Luft | 73/27 |
| 3,064,465 A | * | 11/1962 | Richardson | 73/27 |
| 3,184,954 A | * | 5/1965 | Klein | 73/27 |
| 3,292,421 A | * | 12/1966 | Meyer | 73/27 |
| 3,435,662 A | * | 4/1969 | Meyer | 73/27 |
| 3,471,776 A | * | 10/1969 | Eller et al. | 324/36 |
| 3,504,274 A | * | 3/1970 | Eller et al. | 324/36 |
| 3,616,679 A | * | 11/1971 | Meyer et al. | 73/27 A |
| 4,403,186 A | * | 9/1983 | Kotani et al. | 324/204 |
| 4,563,894 A | * | 1/1986 | Karrer | 73/24 |
| 5,012,669 A | * | 5/1991 | Meyer | 73/25 |
| 5,017,283 A | * | 5/1991 | Oder | 209/212 |
| 5,269,170 A | * | 12/1993 | Meyer | 73/25.02 |

* cited by examiner

Primary Examiner—Hezron Williams
Assistant Examiner—David J. Wiggins
(74) Attorney, Agent, or Firm—Moonray Kojima

(57) ABSTRACT

A magnetic oxygen analyzer which employs a detector comprising a magnetic pole, heat generator arranged in a non-uniform magnetic field where the intensity of a magnetic field produced by the magnetic pole varies, and a magnetic wind sensor disposed to not be affected by heat produced by the heat generator. A change in electrical resistance of the sensor, caused by change in magnetic wind strength, is detected as the oxygen concentration of a mixed gas. The magnetic wind is caused by the magnetic field produced by the magnetic pole and by heat produced by the heater and is related to the oxygen concentration of the mixed gas exposed to the analyzer. Advantageously, the analyzer of the invention provides improved signal to noise ratio, is immune to ambient temperature, and eliminates the need for precise temperature control.

18 Claims, 23 Drawing Sheets

- 1a MAGNETIC POLE
- 2a THERMISTOR (TO GENERATE MAGNETIC WIND)
- 3a THERMISTOR (TO DETECT MAGNETIC WIND)
- 1b MAGNETIC POLE

4 AMPLIFIER

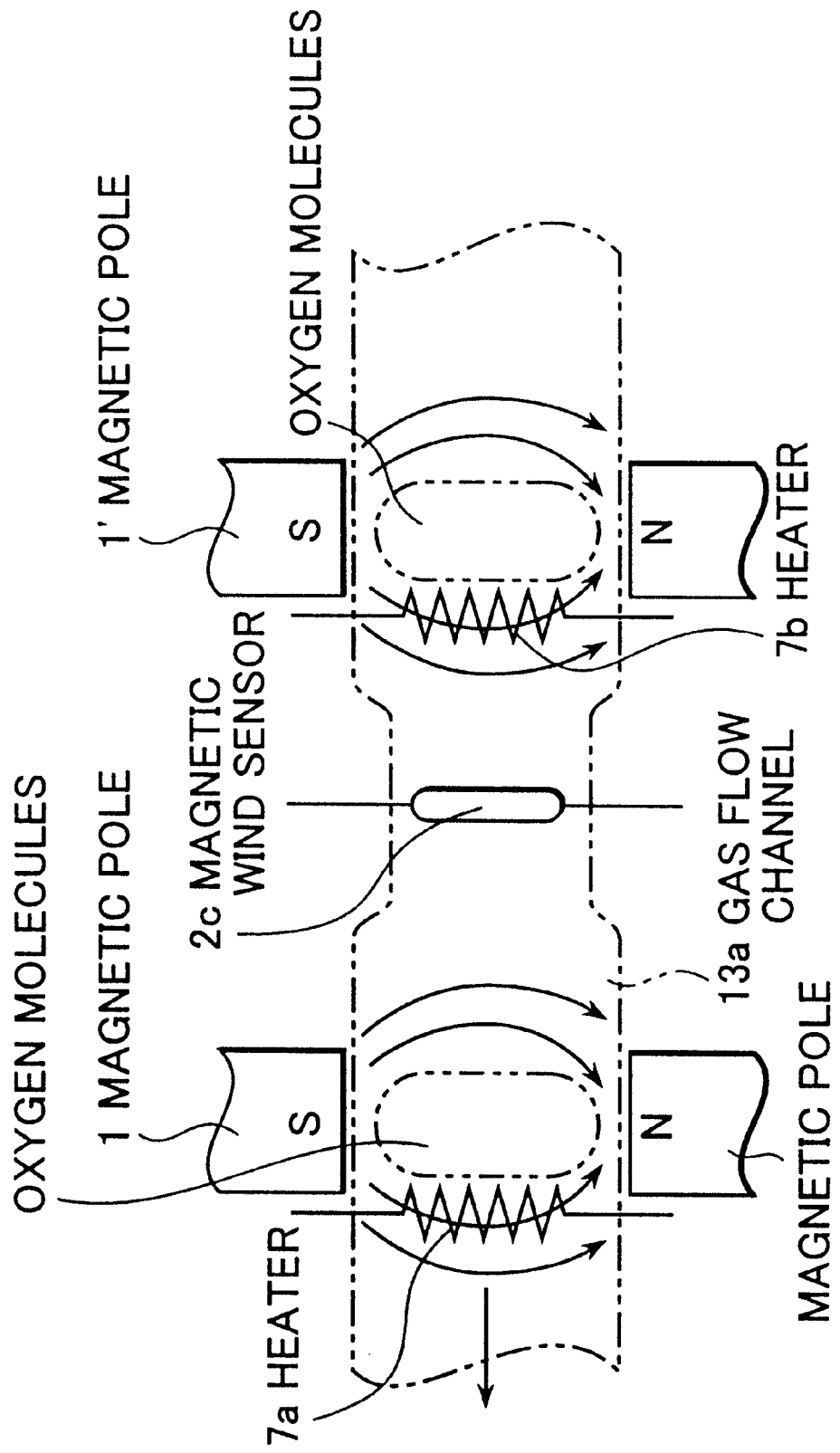

7 HEATER   1c THROUGH HOLE

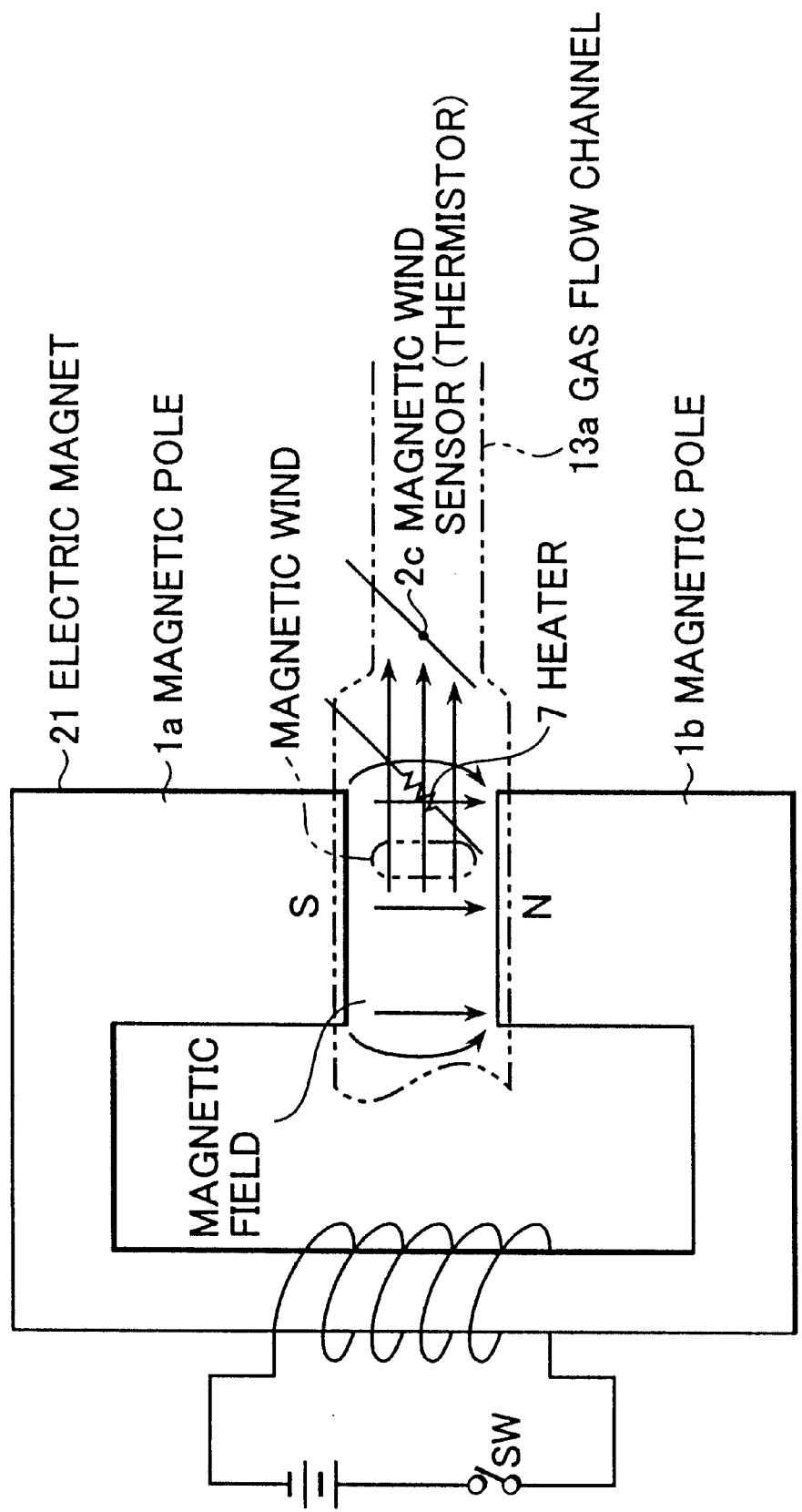

FIG.17
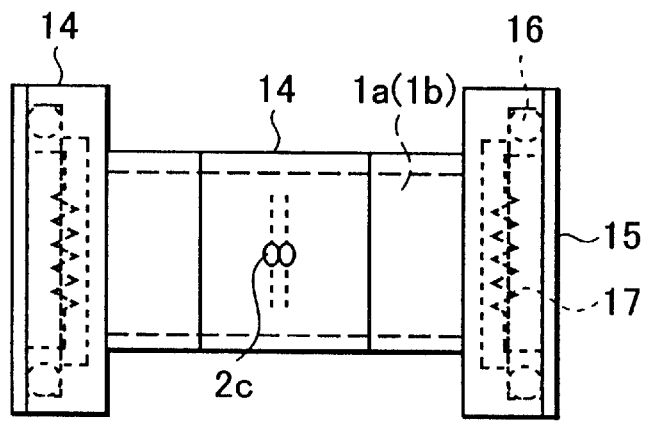
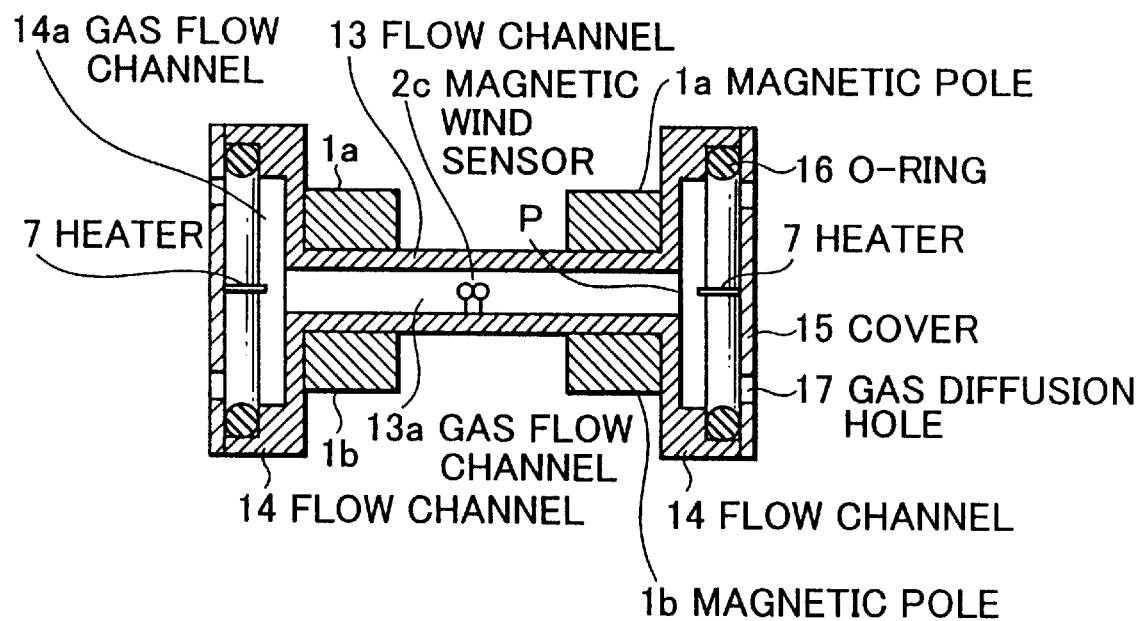
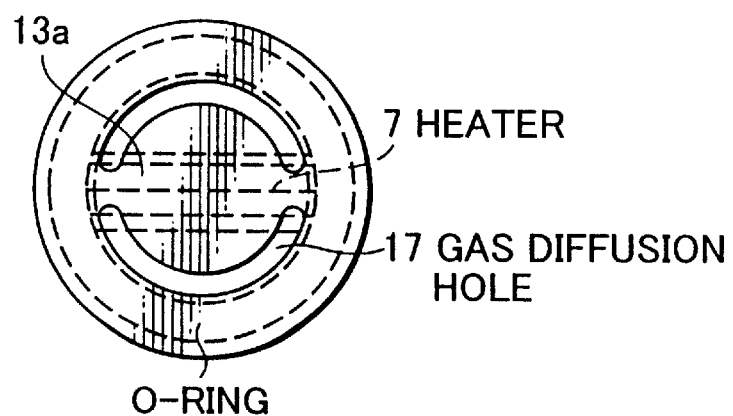

FIG.18
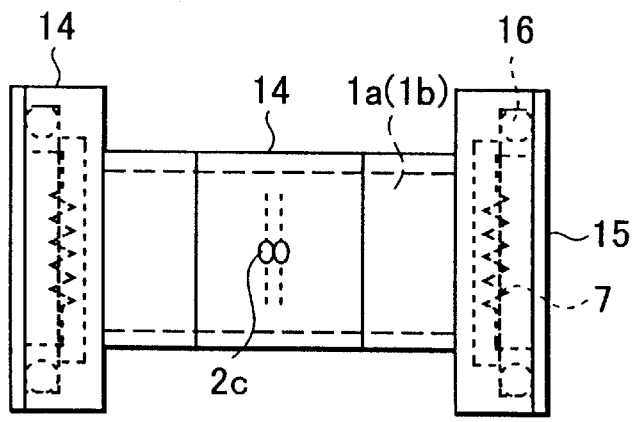
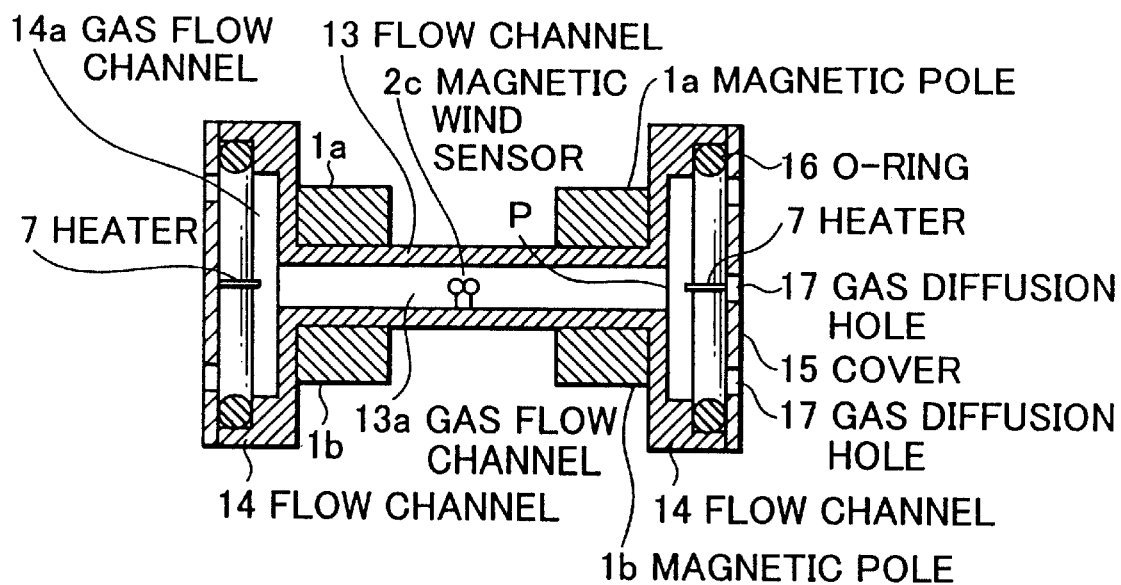
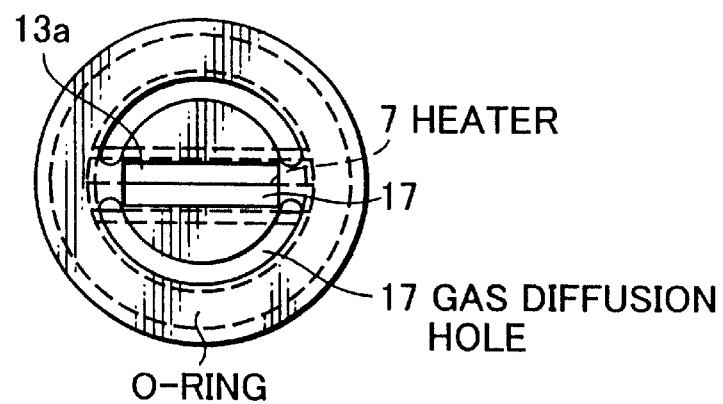

FIG.19
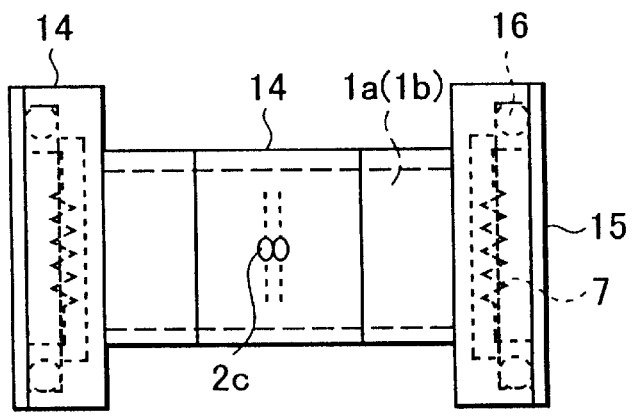
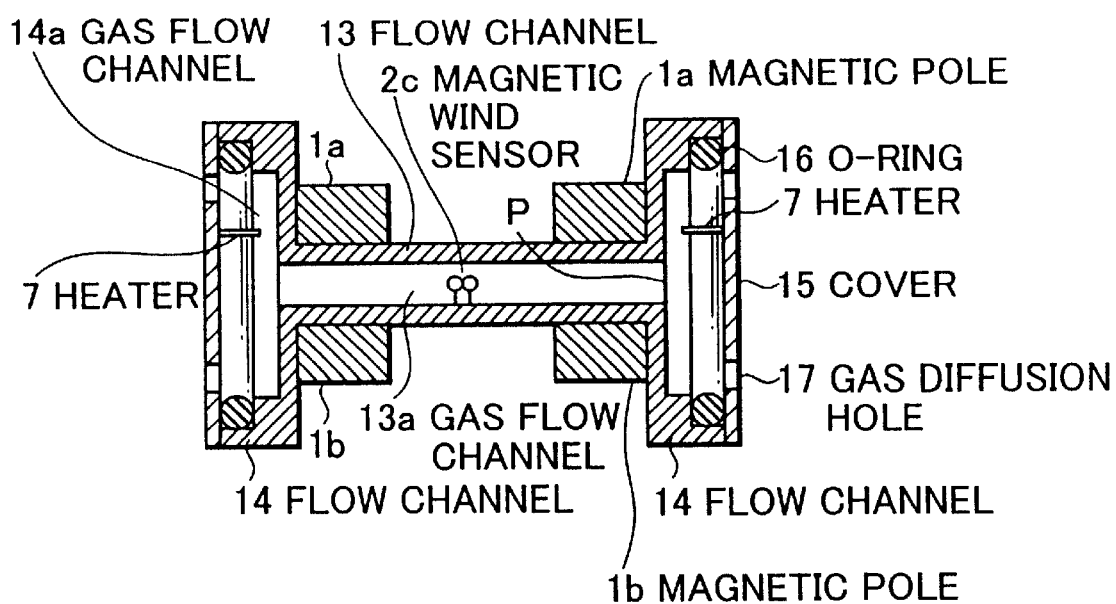
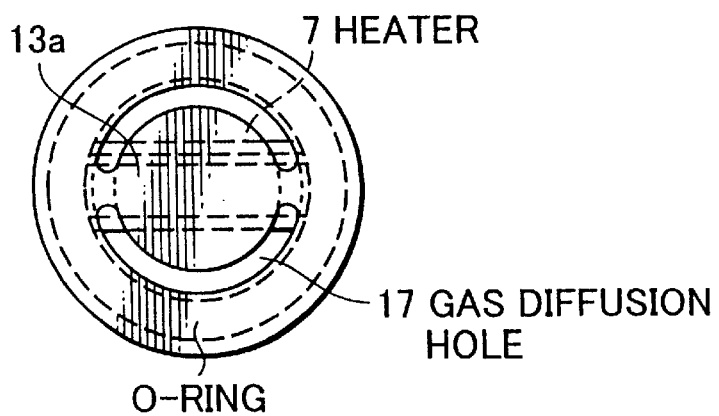

VOLTAGE OF POWER SUPPLY

OUTPUT VOLTAGE (WITH OXYGEN)

OUTPUT VOLTAGE (WITHOUT OXYGEN)

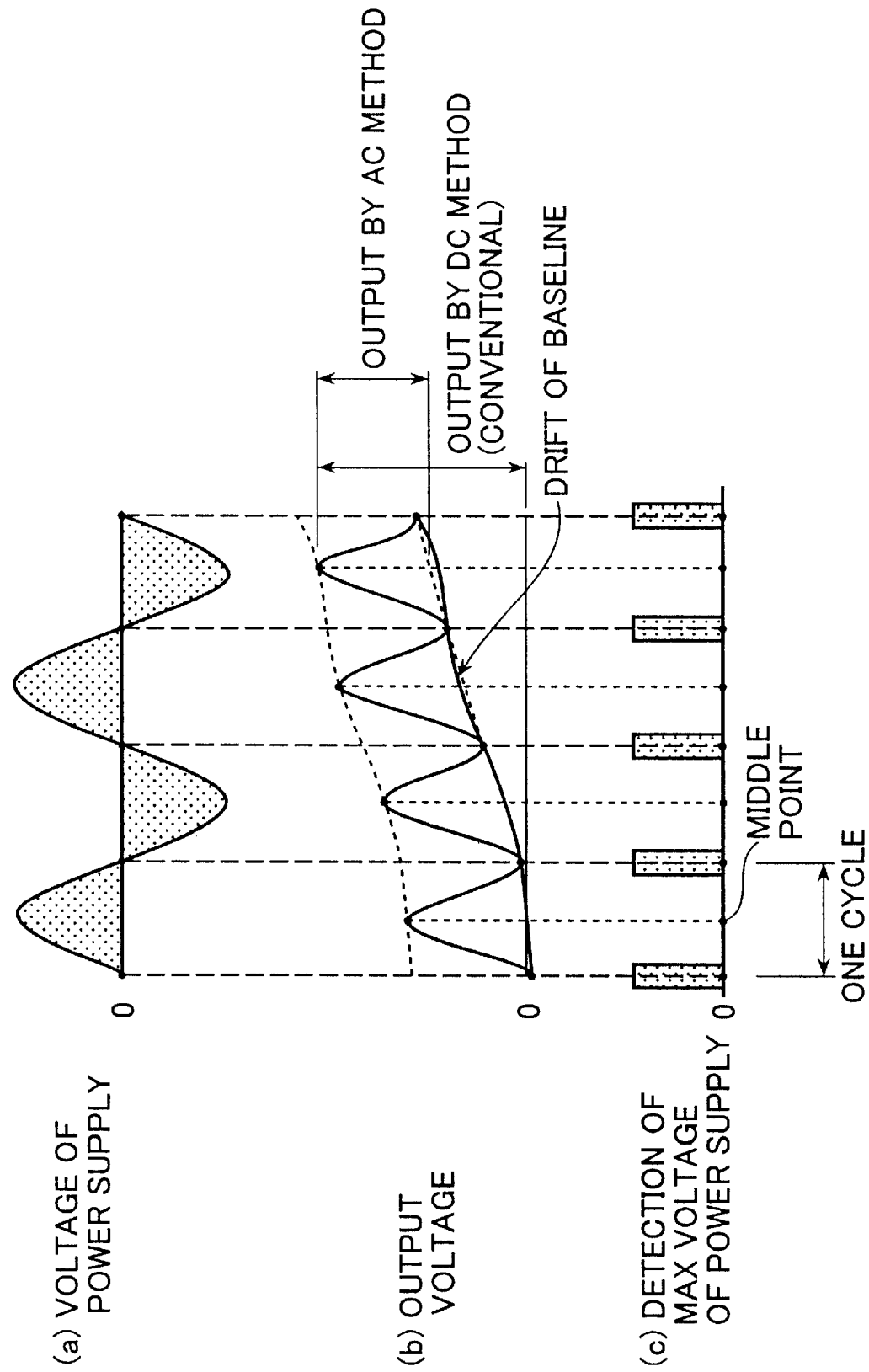

MAGNETIC OXYGEN ANALYZER

BACKGROUND OF THE INVENTION

1. Field of Invention

This invention relates to a magnetic oxygen analyzer for measuring the oxygen concentration of a mixed gas flowing, for example, in a flue, wherein the analyzer provides provides improved signal to noise ratio, improves controllability of thermomagnetic winds, increases immunity to effects of ambient temperature variations, and eliminates need for precise temperature control.

2. Description of the Prior Art

Precise measurement of oxygen concentration of a mixed gas is important for a broad range of processes. Accordingly, in the art, various devices have been devised to effect such measurement; however, much remains to be improved upon.

FIG. 1(A) shows a detector used in the art in a magnetic oxygen analyzer, wherein devices 1a and 1b generate magnetic fields (e.g. permanent magnets), the ends thereof having a specific area and the magnets thereof being oppositely arranged with a specific distance therebetween; thermistors 2a and 2b produce thermomagnetic wind (hereinafter referred to as "magnetic wind") and are arranged in an area where the intensity of magnetic field is caused to vary; and thermistors 3a and 3b are arranged to be external to but close to thermistors 2a and 2b and function to detect magnetic wind. When the magnetic oxygen analyzer of FIG. 1(A) is placed in a mixed gas containing oxygen, the oxygen gas which is a paramagnetic material is gathered into a magnetic field by the magnetic forces. The magnetic susceptibility of the oxygen gas thus gathered is decreased as the gas is heated by thermistors 2a and 2b, which act as heaters, and are arranged in an area having variable intensities of magnetic fields. Hence, a difference occurs between the magnetic susceptibility of the oxygen gas and that of an oxygen gas near the middle of the magnetic field. Accordingly, different magnetic forces act upon the heated and non-heated parts of the oxygen gas, and cause the forces on the different parts to be unbalanced.

There are various ways to arrange devices for generating magnetic fields and for heating. In the device of FIG. 1(A), an oxygen gas, with a greater magnetic susceptibility and located at one edge of a magnetic field, not provided with a heater, is forced to move to a heated edge of the magnetic field. In addition, a low temperature gas is caused to flow into the unheated area with a variable magnetic field intensity from other areas. Hence, a continuous flow of gas occurs.

This gas is proportional to the oxygen concentration of the mixed gas. Hence, the temperature of the thermistor placed close to a hot thermistor is raised, as compared with the temperature thereof, and thereby varying the difference in resistances between the two thermistors.

FIG. 1(B) shows mechanism for eliminating the effects of ambient temperature on the arrangement of FIG. 1(B), by controlling the temperature of the oxygen sensing element. In the circuit diagram, a constant temperature bridge is formed by resistors Rc, Rd and Rs; and a bridge comprising thermistors 2a, 2b, 3a and 3b, and resistors Ra and Rb. A variable resistor Rt is used for bridge temperature control. An amplifier 4 detects an electrical imbalance, if any, between contacts X and y, and drives a series connected transistor 5 to cancel the imbalance by changing the bridge current.

In the above arrangement, two pairs of a heat generating element and a heat sensing element are provided in the area with a variable magnetic field intensity. Hence, it is possible to reduce detection errors even when the magnetic oxygen analyzer is installed in a tilted position.

The resistance and temperature coefficient, also known as the B constant, of the thermistors varies from thermistor to thermistor. Accordingly, the resistance of thermistors 2a, 2b, 3a and 3b will vary at different rates of change according to ambient temperature variations. Thus, the output voltage that developes across the output terminals of the bridge circuit will have different temperature coefficients, depending on the combination of thermistors used. Thus, the detector, including the thermistors, require strict temperature control. This results in a problem with conventional analyzers, namely, such conventional analyzers will require a large scale, precise thermostatic chamber. Other problems with conventional magnetic oxygen analyzers are that the bandwidth of noise is comparatively wide, and that such conventional device use DC detection methods. Thus, the signal to noise ratio (S/N) is poor.

Accordingly, it can be understood that the prior art can be considerably improved upon.

SUMMARY OF THE INVENTION

An object of the invention is to overcome the aformentioned problems, deficiencies, and disadvantages of the prior art.

The invention provides a magnetic oxygen analyzer having a detector comprising a magnetic pole from oppositely arranged magnetic poles, heat generation means arranged in an area of non-uniform magnetic fields, where the intensity of a magnetic field produced by the magnetic pole is caused to vary, and a magnetic wind sensor disposed in a position whereat the sensor is not affected by heat produced by the heat generation means. A resistance change in the magnetic wind sensor, caused by change in the strength of the magnetic wind, is detected as the oxygen concentration in the mixed gas. The magnetic wind occurs by the magnetic field produced by the pole being heated by the heat generation means with the mixed gas being exposed to the analyzer and the magnetic wind then is exposed to the magnetic wind sensor.

Accordingly, the magnetic oxygen analyzer of the invention makes it possible to produce a higher volume of magnetic wind, reduce the noise bandwidth, and thereby improve the S/N ratio, and eliminate the need for precise temperature control.

BRIEF DESCRIPTION OF THE DRAWINGS

FIG. 7 is a schematic view depicting another illustrative embodiment of a magnetic oxygen analyzer of the invention, wherein devices for generating magnetic fields and for generating heat are arranged so as to sandwich a magnetic wind sensor.

FIG. 9 is a schematic view depicting still another illustrative embodiment of the invention, wherein an electric magnet provides the magnetic pole.

FIG. 17 is a schematic view depicting a further illustrative embodiment of the invention, wherein, noise in detected signals due to thermal shock waves, is reduced.

FIG. 18 is a schematic view depicting another illustrative embodiment, wherein noise in detected signals due to thermal shock waves, is reduced.

FIG. 19 is a schematic view depicting another illustrative embodiment of the invention, wherein noise in a detected signal due to thermal shock waves, is reduced.

FIG. 23 is a chart depicting the state of detector output when a zero point drift occurs.

DETAILED DESCRIPTION OF THE PREFERRED EMBODIMENTS

Figure 1A:
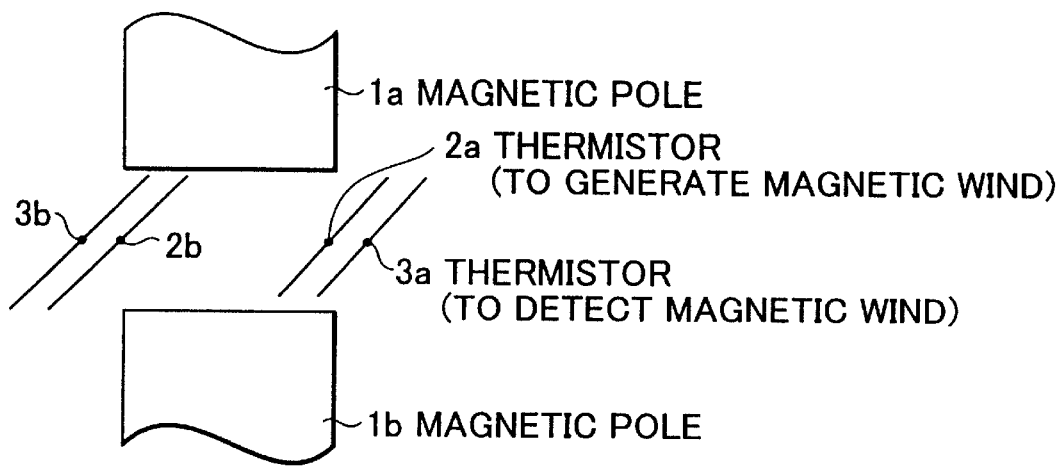
FIGS. 1(A) and 1(B) are schematic views depicting a detector used as a magnetic oxygen analyzer and a circuit diagram of the detector.
Figure 1B:
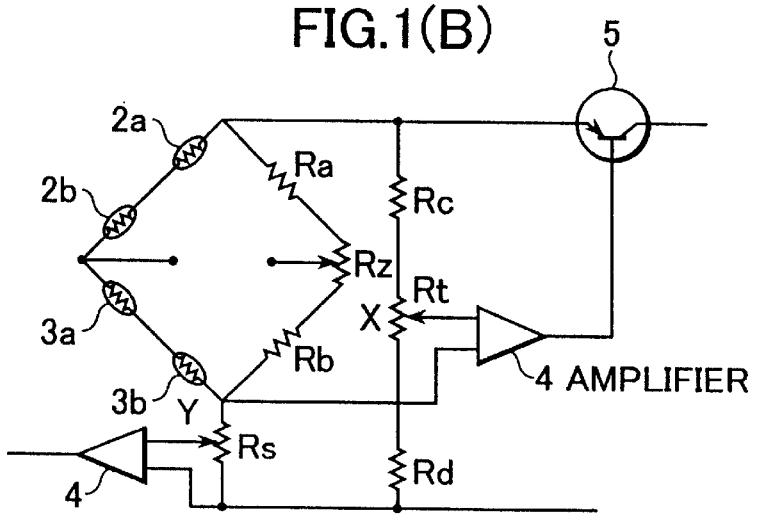
Figure 2A:
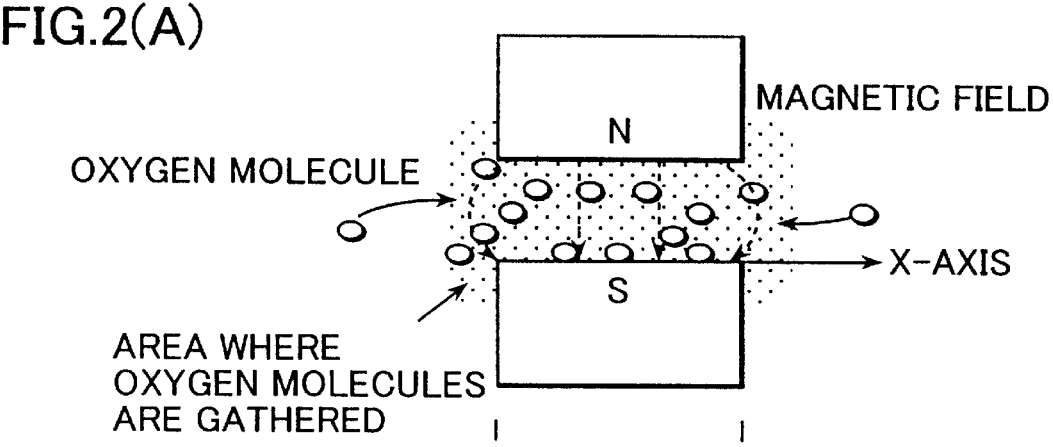
FIGS. 2(A)–2(C) are schematic views for explaining the measurement principle of the magnetic oxygen analyzer of the invention.
Figure 2B:
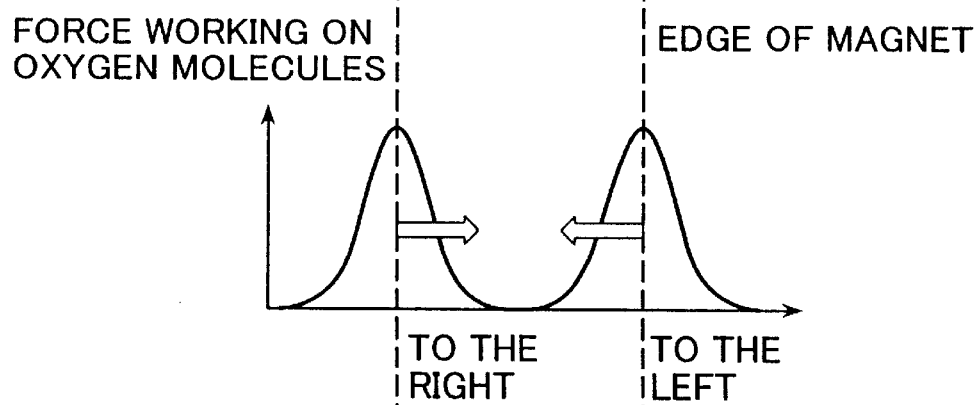

The principle of measuring the oxygen content of a gas will be described briefly with reference to FIGS. 2(A), 2(B), 2(C), 3(A), 3(B) and 3(C), wherein FIG. 2(A) shows the relationship between oxygen molecules and magnetic fields when a magnetic pole is disposed in a gas containing oxygen. In this case, an X-axis force F acting on the oxygen molecule can be represented by the following:

$$F = \chi \cdot (\partial H / \partial X) \cdot H$$

wherein ω is the magnetic susceptibility of oxygen, H is the intensity of a magnetic field, and $\partial H/\partial X$ is the rate of change of magnetic field. Accordingly, a force which attracts oxygen molecules acts on an area, e.g. non-uniform magnetic field, where the magnetic field is intense and the intensity varies, as shown in FIG. 2(B). In addition, the balance of forces is achieved as forces acting toward the left and right, act upon each other at the edges of a magnetic pair.

Figure 2C:
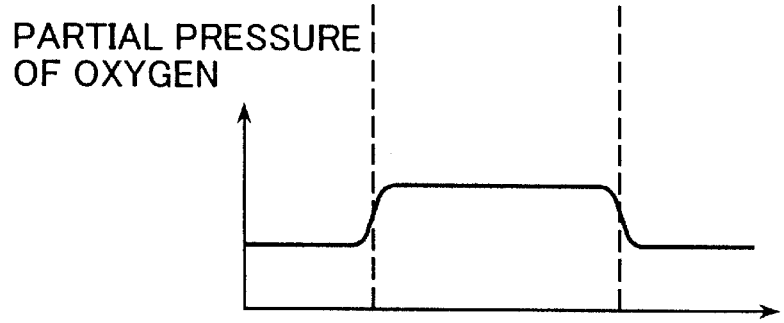

FIG. 2(C) shows the case where the partial pressure, e.g. concentration of oxygen, is higher within the magnetic field, e.g. the gap between the magnets, where oxygen molecules are gathered, than in the area surrounding the magnetic field.

Figure 3A:
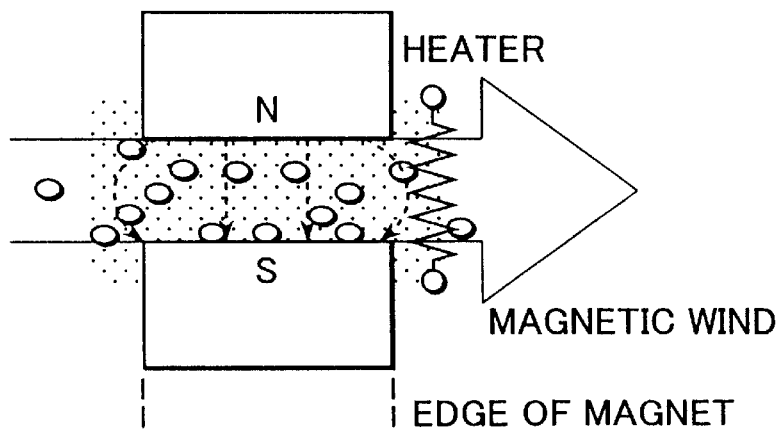
FIGS. 3(A)–3(C) are schematic views for explaining the measurement principle of the magnetic oxygen analyzer of the invention.
Figure 3B:
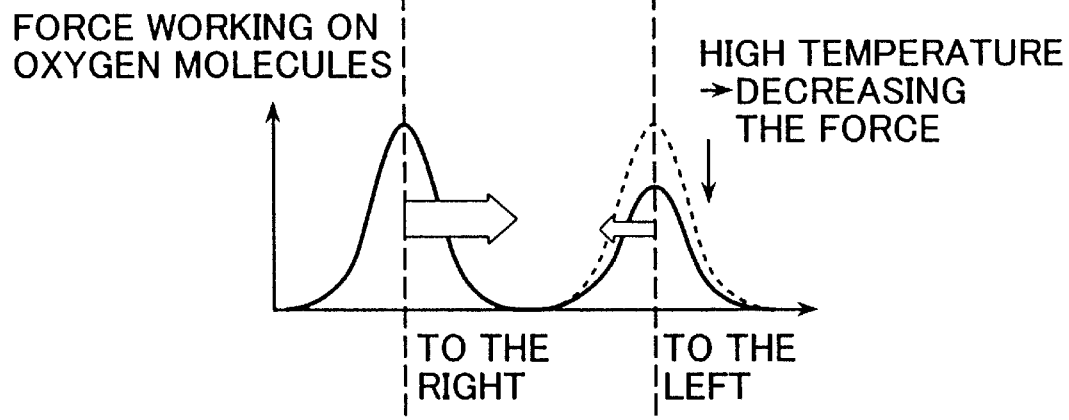

FIGS. 3(A) and 3(B) show the case where a heater is placed at the right side edge of the magnetic field, e.g. next to the magnet poles, whereby the magnetic susceptibility of oxygen is varied. Only the right side edge is heated to reduce the force acting toward the left, so that the partial pressure of oxygen becomes unbalanced.

Figure 3C:
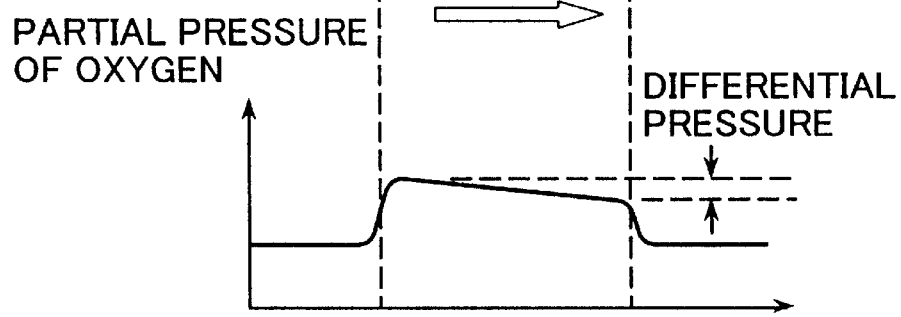

FIG. 3(C) shows the case where the partial pressure of oxygen is unbalanced. Hence, a pressure difference is produced, thereby to cause a rightward magnetic wind to blow. This pressure difference, i.e. strength of the magnetic wind, is determined by the oxygen concentration, magnetic field intensity, and the amount of heat produced by-the heater.

Figure 4:
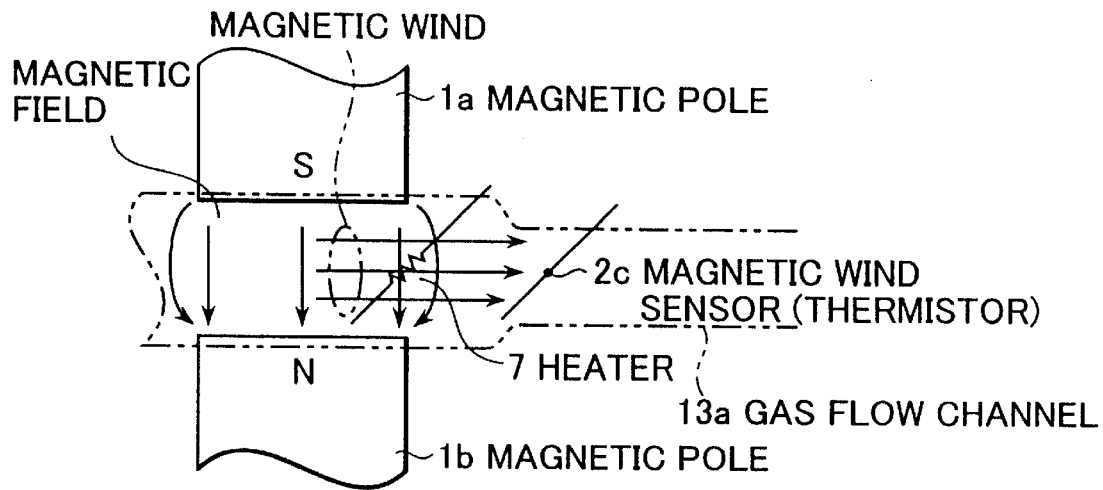
FIG. 4 is a schematic view depicting one illustrative embodiment of the detector used in the magnetic oxygen analyzer of the invention.
Figure 5A:
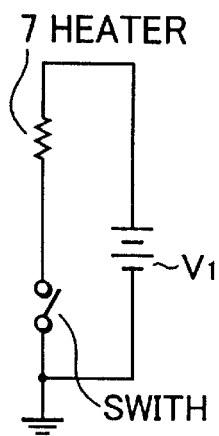
FIGS. 5(A) and 5(B) are circuit diagrams depicting one illustrative embodiment of circuit diagrams of the magnetic oxygen analyzer of the invention.
Figure 5B:
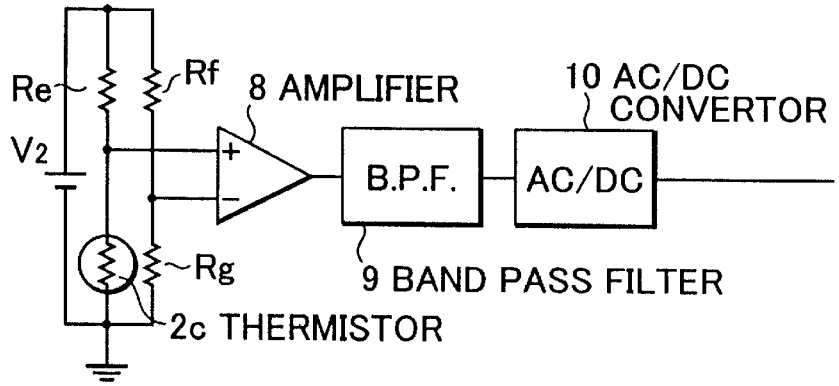

FIG. 4 shows an enlarged view of a detector used in the magnetic oxygen analyzer of the invention. FIGS. 5(A) and 5(B) are circuit diagrams of the detector of FIG. 4. Magnetic pole 1 comprises opposite magnetic poles 1a, and 1b, wherein the edges thereof have specific areas and are arranged with a specific gap formed therebetween. A heater 7, e.g. made of metal resistance wire or sintered metal oxide element, functions as a heat generator. A metal resistance wire 2C or sintered metal oxide element, e.g. thermistor, functions as a magnetic wind sensor. These components are arranged in an area where the intensity of a magnetic field is varied. Although these components are arranged on the right of the magnetic poles, the components may be placed on the left of the magnetic poles, or on both sides thereof separately, or in any other suitable position as long as they are not affected by the heat. An area enclosed by the double dashed lines indicates a gas flow channel 13a.

In the detector of FIG. 4, an oxygen gas is gathered into a magnetic field by means of magnetism, according to the principles of operation, discussed above, when the detector is placed in a mixed gas containing oxygen. Hence, a difference in pressure occurs between the oxygen gas within the magnetic field and oxygen gas located outside the magnetic field. When the oxygen gas, thus gathered, is heated by heater 7 within the area where the magnetic field intensity is varied, the magnetic susceptibility of the oxygen gas is decreased and a magnetic wind is caused to occur in the direction indicated by the arrows. Hence, heat is removed from the metal resistance wire or sintered metal oxide element 26c, which serves as the magnetic wind sensor (also referred to as thermistor) by the magnetic wind produced in proportion to the oxygen concentration of the mixed gas. Thus, the thermistor 2c is cooled to cause the resistance thereof to be changed.

FIGS. 5(A) and 5(B), considered together, depict a detector circuit for detecting a resistance change in thermistor 2c, wherein FIG. 5 (A) is a circuit for turning ON and OFF heater 7 at fixed intervals and FIG. 5(B) is a circuit wherein the resistance of thermistor 2c is incorporated at one of the resistances comprising a Wheatstone bridge (referred to as a bridge). In FIG. 5(B) resistnaces Re, Rf and Rg are known resistances. A current that flows as resistance of thermistor 2c is changed, is amplified by amplifier 8, then made to pass through a band pass filter 9 and then converted from AC to DC by an AC/DC converter 10. The AC/DC converter 10 is intended to rectify and smooth a detected signal that passes through the band pass filter 9. In such a process, band pass filter 9 filters a current flowing through the bridge in synchronism with an interval at which the heater 7 is turned ON and OFF. According to the detector, effects of the ambient temperature that is varied at relatively long intervals are eliminated by the low pass filter fo band pass filter 9. Similarly, high frequency noise super-imposed on the detected signal is removed by the high pass filter of the band pass filter 9.

Thus, it is possible with the invention to eliminate the need for a conventional precision thermostatic chamber by keeping the detected signal to within a specific band of frequencies. In other words, a simple thermostatic chamber will suffice in this case. Also, a magnetic wind is produced with a heater and temperature detection is achieved by use of a thermistor. Thus, it is possible with the invention to easily control the strength of the magnetic wind.

Figure 6A:
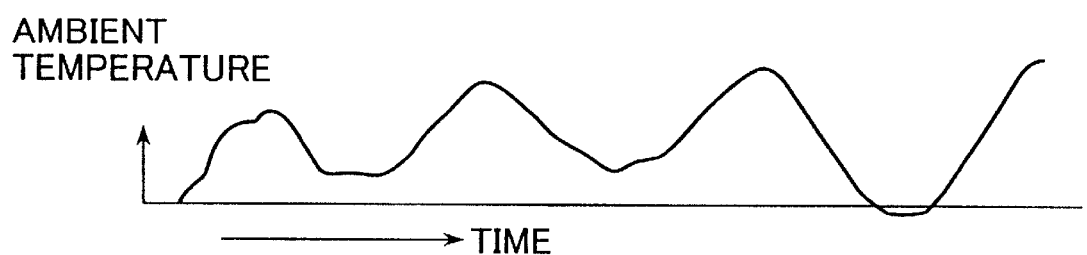
FIGS. 6(A) and 6(B) are schematic graphs depicting an example of detector output wherein a band pass fileter is driven in synchronism with an ambient temperature variation and the ON-OFF timing of a heater.
Figure 6B:
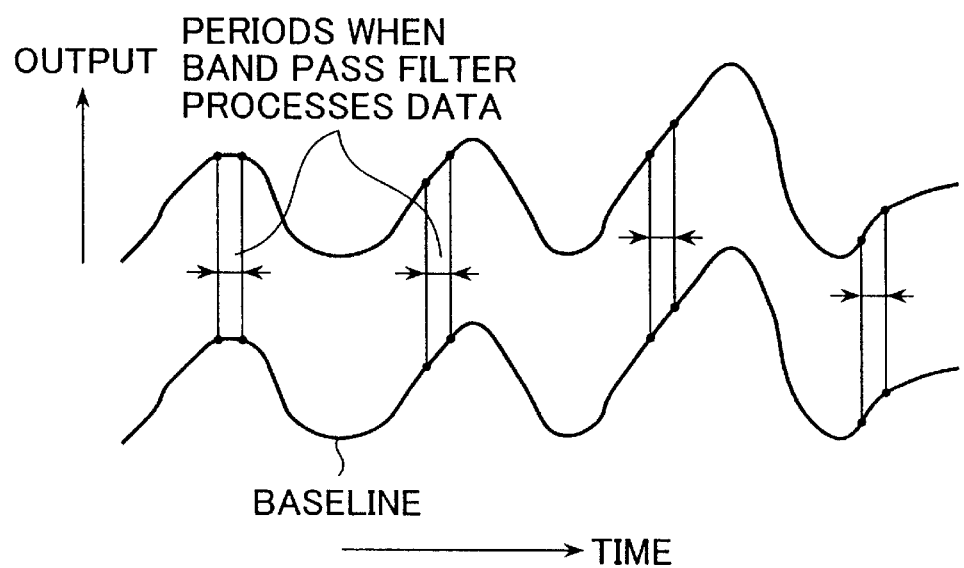

FIGS. 6(A) and 6(B) are graphs for explaining an example of a detector output, wherein FIG. 6(A) shows when the gate of a band pass filter is opened and closed in synchronism with a variation the ambient temperature with time, and the ON/OFF timing of a heater; and wherein FIG. 6(A) shows variations of ambient temperature with time. As can be understood from FIGS. 6(A) and 6(B), the temperature based variation in the detector output is reduced since measurement is performed during a short length of time in which the gate is open.

FIG. 7 shows another embodiment wherein devices for generating magnetic fields 1, 1' which are configured alike are arranged so as to sandwich the magnetic wind sensor 2c. In addition, heat generator means comprising first heater 7a and second heater 7b are arranged in two locations in an area with a variable magnetic field intensity (i.e. on the left edge of each magnetic pole in this case). The heaters 7a, and 7b are turned ON and OFF at the same time, in order to increase the volume of magnetic wind by flowing oxygen gases gathered in the areas labelled "Oxygen Molecules", in the direction indicated by the arrows pointing left so that the sensitivity of the magnetic wind sensor 2c is increased. In this embodiment, devices for generating magnetic fields, which may be of the same configuration, may be arranged in two or more locations on both sides of the magnetic wind sensor 2c. The circuits for turning ON/OFF the heaters and for detecting a resistance change in the magnetic wind sensors are the same as those shown in FIGS. 5(A) and 5(B).

Figure 8A:
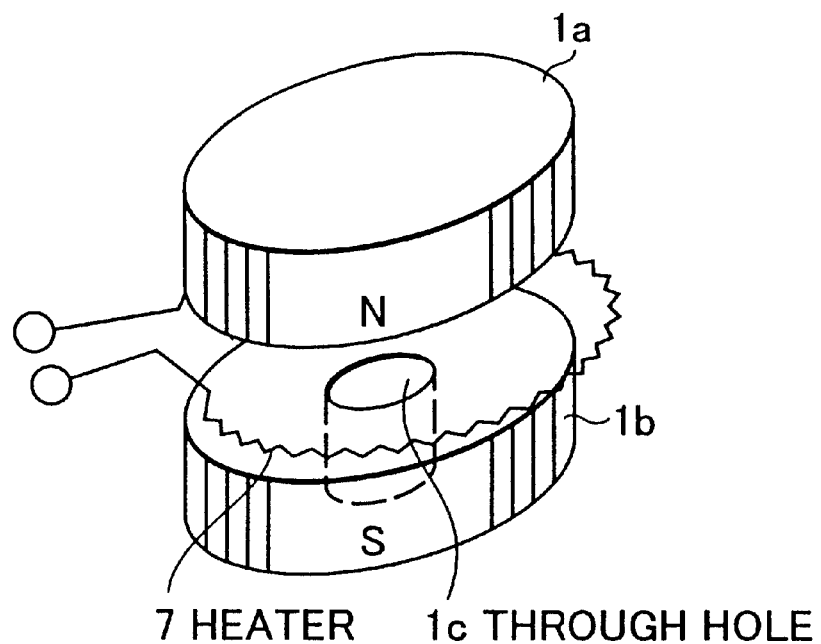
FIGS. 8(A) and 8(B) are schematic views depicting yet another illustrative embodiment wherein a circular magnetic pole is provided and wherein a heat means is formed around the circumference to the magnetic pole.
Figure 8B:
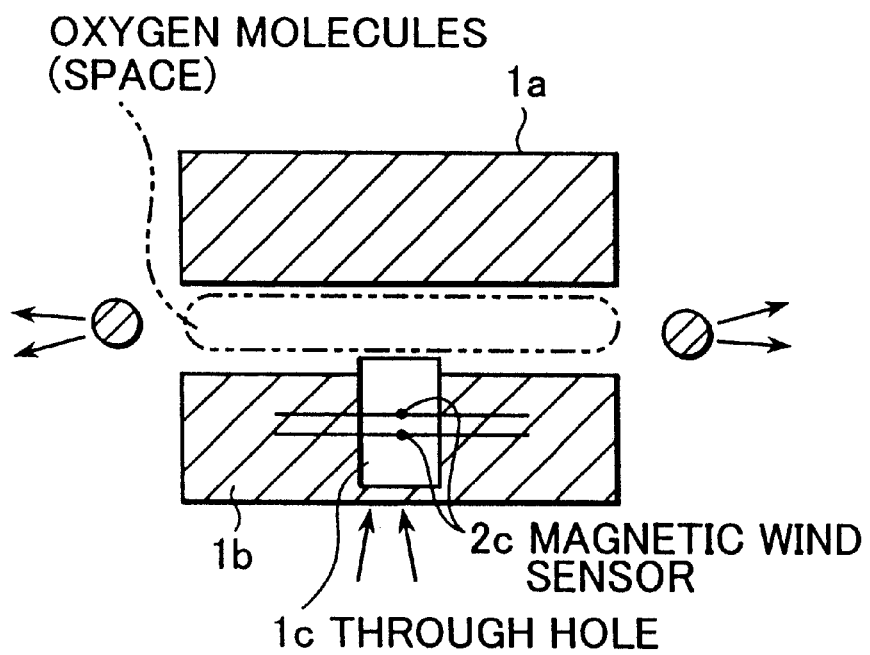

FIGS. 8(A) and 8(B) show another embodiment of a magnetic oxygen analyzer, wherein devices for generating magnetic fields 1a and 1b, such as circular plates, are provided and heater 7 is formed around the circumference of the magnetic pole, or magnetic field. Formed near the center of one magnetic pole is a through hole 1c leading into a space labelled "Oxygen Molecule Space" one end of which is enclosed by heater 7. Magnetic wind sensors 2c are provided inside through hole 1c or in the vicinity thereof.

When the detector of FIGS. 8(A) and 8(B) is placed in a gas atmosphere containing oxygen, oxygen molecules which contribute to the oxygen concentratioin are gathered into the space labelled "Oxygen Molecule Space". The balance of pressure is lost when heater 7 is turned ON, causing the oxygen molecules to flow from the magnetic poles in the direction of the arrows (not labelled) as shown in FIG. 8(B). The oxygen molecules thus driven out of the space are once again gathered by way of through hole 1c. This flow of oxygen is detected by magnetic wind sensors 2c which are disposed around the midpoint of through hole 1c so as to be perpendicular to the direction of flow and parallel with and close to each other.

The reason why the two magnetic wind sensors 2c are disposed around the midpoint of through hole 1c so as to be perpendicular to the direction of flow and parallel with and close to each other, is that changes in the detector output caused by disturbances other than magnetic wind, need to be cancelled.

Note that in this embodiment, the circuits for turning ON/OFF heater 7 and for detecting changes in the resistances of the magnetic wind sensors are the same as those in the embodiment of FIGS. 5(A) and 5(B).

FIG. 9 shows another illustrative embodiment of a magnetic oxygen analyzer of the invention, wherein an electric magnet 21 is used in place of the permanent magnet of FIG. 4. A magnetic field is turned ON and OFF by turning ON and OFF an electric current applied to electric magnetic 21 at fixed intervals by means of switch SW. Heater 7 is not turned ON/OFF in this case, however. A magnetic wind corresponding to the oxygen concentration is produced on an intermittent basis, by turning ON/OFF switch SW and hence the magnetic field.

The circuit for detecting the magnetic wind is the same as that shown in FIG. 5(B). In addition, an electric current, which flows as the resistance of thermistor 2c is changed, is amplified by amplifier 8, made to pass through band pass filter 9, and then AC/DC converted. In the foregoing embodiment, it is also possible to obtain a detector output which is immune to ambient temperature, by turning ON/OFF a magnetic field and by letting the resulting electric current pass through band pass filter 9.

As indicated in FIGS. 4, 7 and 9, using double dashed lines, it is possible to increase the flow speed of a magnetic wind by narrowing the gas flow channel 13a at some midpoint thereof, such as by placing the heat generator 7 of the magnetic oxygen analyzer in the larger diameter portion of the channel, and then the magnetic wind sensor 2c, comprising a thermistor, in the smaller diameter poriton of channel 13a. Accordingly, it is possible to increase the sensitivity of the magnetic wind sensor or thermistor 2c.

Figure 10A:
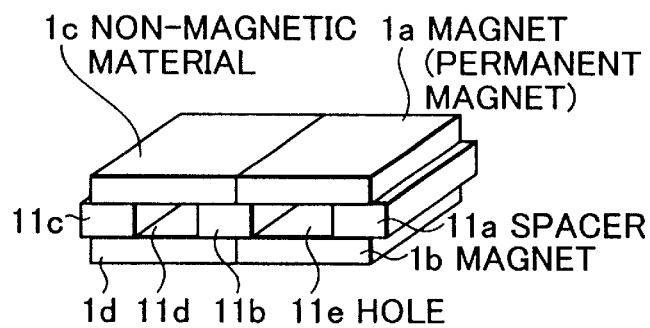
FIGS. 10(A) and 10(B) are schematic views depicting a further illustrative embodiment of the invention, wherein permanent magnets are oppositely arranged with a space therebetween and where in non-magnetic materials of the same configuration are provided adjacent the permanent magnets.
Figure 10B:
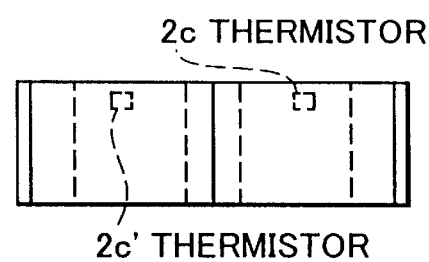

FIGS. 10(A), and 10(B) show another embodiment of the magnetic oxygen analyzer of the invention, wherein FIG. 10(A) is an enlarged perspective view and FIG. 10(B) is a plan view. In this embodiment, permanent magnets 1a are arranged opposite each other with a plurality of spacers 11a, 11b, and 11c disposed therebetween and non-magnetic materials 1c, having the same construction as that of the permanent magnets 1a, are disposed adjacent the magnets. The area of a hole 11d, between spacers 11b and 11c, and the area of a hole 11e between spacers 11b and 11a are designed to be the same so that the same amounts of gas will flow therethrough. The thermistors 2c (see FIG. 10(B)) is disposed in the gas flow channel on the side of permanent magnets 1a and 1b at a point near both ends of a magnetic field. Another thermistor 2c' is disposed in the gas flow channel on the side of non-magnetic materials 1c and 1d at a point correspoinding to the thermistor 2c positioned on the permanent magnet side.

According to the embodiment, a magnetic wind due to the self heating of a thermistor and a resistance change due to effects of ambient temperature, are produced in thermistor 2c on the permanent magnet side. In contrast, only a resistance change due to effects of ambient temperature is produced in thermistor 2c' on the non-magnetic material side.

Figure 11:
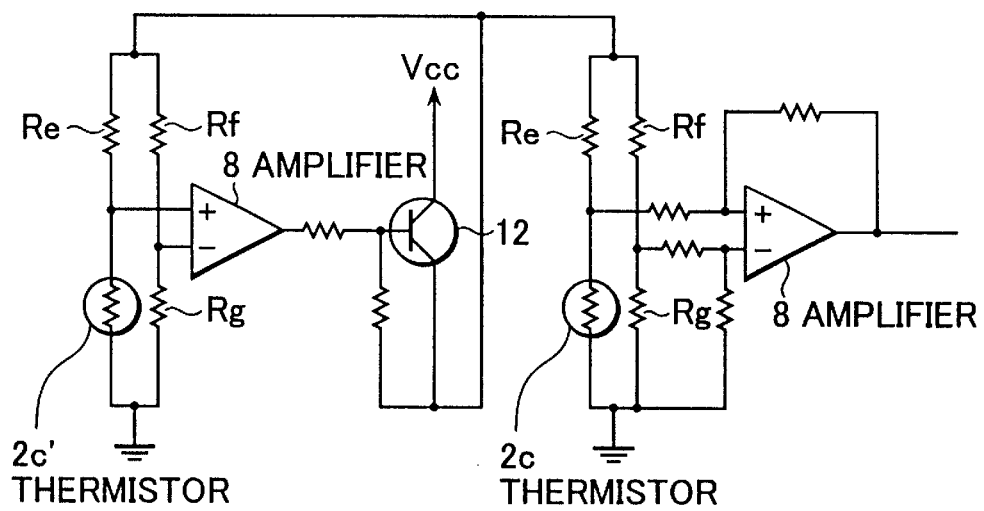
FIG. 11 is a circuit diagram of anther illustrative embodiment of the invention, wherein a bridge circuit on the non-magnetic material side is controlled at a constant temperature and the resulting control voltage is applied to a bridge circuit on the magnet side.

FIG. 11 is a circuit diagram of the embodiment of FIG. 10, wherein a bridge circuit comprising thermistor 2c' and resistances Re, Rf and Rg on the non-magnetic material side (to left)is controlled to be at a constant temperature and the resulting control voltage is applied to a bridge circuit comprising thermistor 2c and resistances Re, Rf and Rg on the permanent magnet side (to right). In this bridge, thermistor 2c is controlled so that Re·Rg=Rf·2c holds true. A transistor 12 is included to power amplify the output of an amplifier 8. The resistance of a thermistor changes since a flow occurs in a mixed gas depending on the attitude in which the detector is installed. According to the embodiment, however, it is possible to cancel measurement errors in the bridge output on the magnet side due to ambient temperature variations or attitudinal errors. Hence, it is possible to provide a signal that is based on magnetic wind and sensitive only to oxygen concentration.

Figure 12:
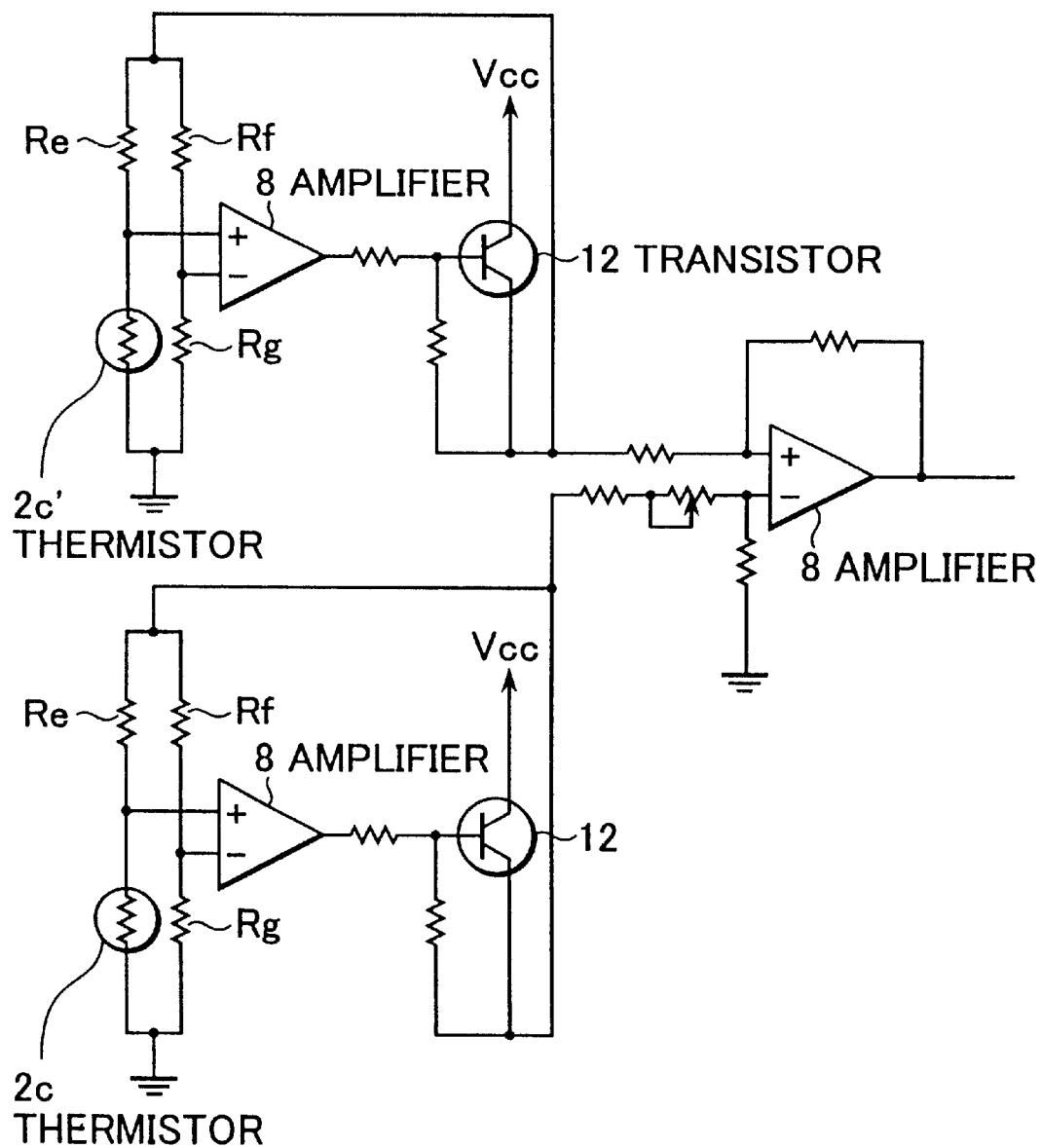
FIG. 12 is a circuit diagram depicting a further illustrative embodiment of the invention, wherein both the non-magnetic and magnet side are controlled at a constant temperature and the resulting output signal is detected by a differential amplifier.

FIG. 12 is a circuit diagram of another circuit used in the embodiment of FIG. 10, wherein both the non-magnetic material side and the magnet side are controlled to be at constant temperatures and the resulting output signal is detected by a differential amplifier. Also, in this circuit, it is possible to cancel measurement errors due to ambient temperature variations or attitudinal errors. Hence, it is possible to provide a signal that is based on magnetic wind and sensitive only to the oxygen concentration.

Figure 13:
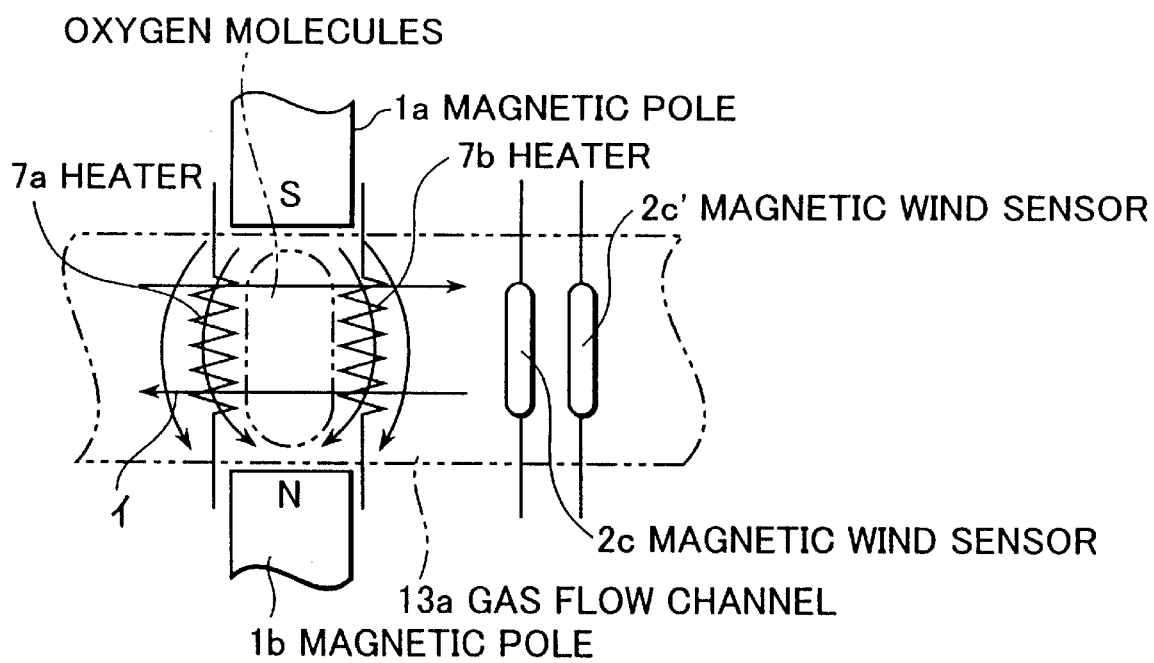
FIG. 13 is a schematic view depicting another illustrative embodiment of the invention, wherein heaters are disposed in areas where the magnetic field intensity is varied.

FIG. 13 shows another embodiment of the magnetic oxygen analyzer of the invention, comprising permanent magnets 1a, and 1b of a magnetic pole formed by oppositely arranged magnetic poles; first heater 7a, second heater 7b arranged in areas where the intensity of an electric field is varied, first magnet wind sensor 2c, and second magnetic wind sensor 2c', one of the magnetic wind sensors being disposed upstream of a magnetic wind flowing through the gas flow channel 13a and the other being disposed downstream thereof.

In the embodiment of FIG. 13, the first and second heaters are turned ON alternately at a frequency of, for example, 1 Hz by means of a heating circuit not shown. The resulting magnetic wind flows in the direction of the arrow pointing right when the first heat 7a is kept ON or in the opposite direction of the arrow, pointing right, when the second heater 7b is kept ON. In this case, the output, i.e. resistance change, of the two magnetic wind sensors 2c and 2c' largely differ from each other.

Figure 14A:
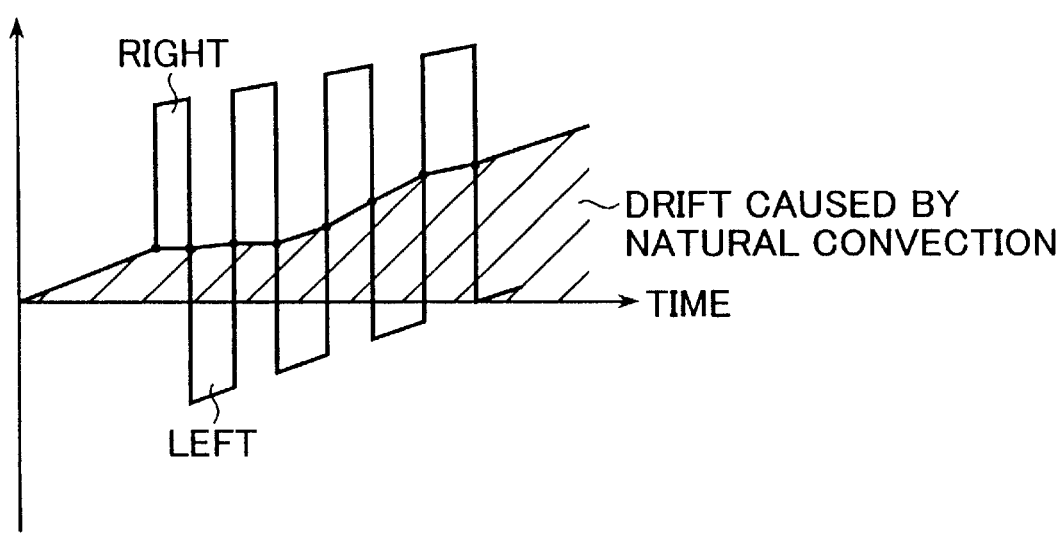
FIGS. 14(A) and 14(B) are graphs depicting the output characteristics of the two magnetic wind sensors of FIG. 13.

FIG. 14(A) shows the output characteristics of the first and second magnetic wind sensors 2c and 2c'. The shaded area is a drift caused by natural convection or a variation in ambient temperature. The line segment graph represents the output of the first and second magnetic wind sensors, wherein the output polarity varies depending on the direction of the magnetic wind.

Figure 14B:
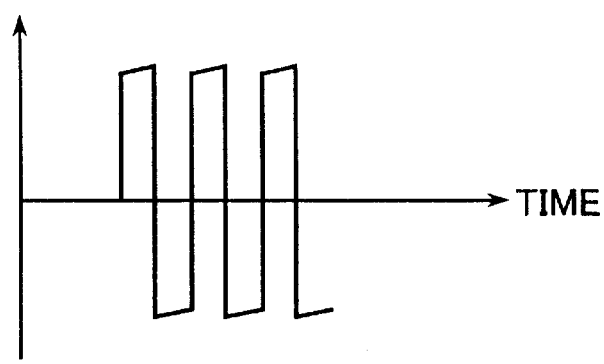

FIG. 14(B) shows the output characteristics where the output of one magnetic wind sensor is subtracted from the output of the other wind sensor, thereby to eliminate effects on the baseline voltage due to disturbances.

Figure 15:
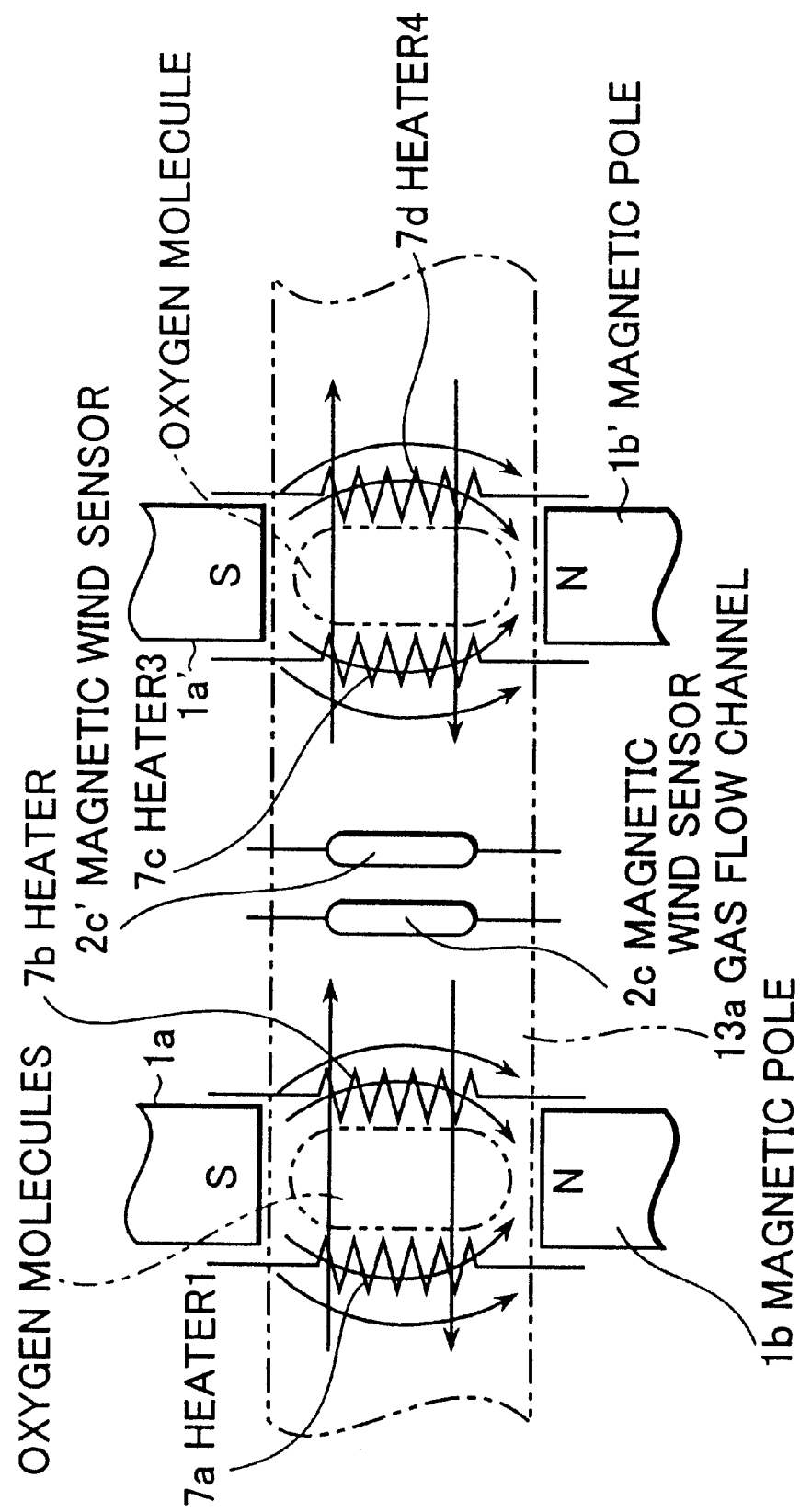
FIG. 15 is a schematic view depicting another illustrative embodiment of the invention, wherein devices for generating magnetic fields and devices for generating heat are arranged so as to sandwich magnetic wind sensors, and are turned ON and OFF alternately.

FIG. 15 shows yet another embodiment wherein in addition to the first pair of magnets 1a and 1b, and first heater 7a, second heater 7b, the embodiment comprises a second pair of permanent magnets comprising devices for generating magnetic fields 1a' and 1b' and heat generating means comprising a third heater 7c and fourth heater 7d, which are of the same construction, and are arranged so as to sandwich magnetic wind sensors 2c and 2c'. First heater 7a and third heater 7c are grouped as one combination and second heater 7b and fourth heater 7d are grouped as another combination. The two combinations are turned ON and OFF alternately so that oxygen gas molecules are gathered into the areas labelled "Oxygen Molecules" flow in the direction of right arrows or left arrows and the volume of magnetic wind is increased, whereby the sensitivity of the magnetic wind sensor is incresaed. The circuit for turning ON the heaters and detecting resistance change in the magnetic wind sensors and the results of detection by the circuit are basically the same as the circuit shown in FIG. 12 and the detection results provided thereby, though the substantial output values differ from each other.

Figure 16A:
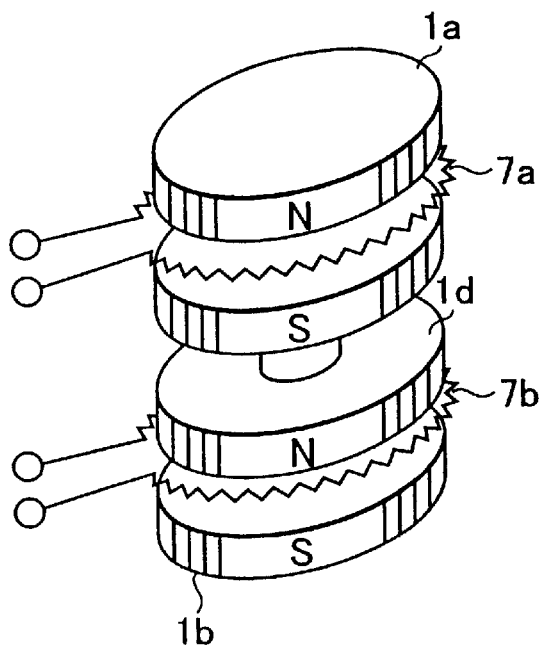
FIGS. 16(A) and 16(B) are schematic views depicting yet another illustrative embodiment of the invention, wherein an additional permanent magnet is placed on each side of a permanent magnet with the polarities thereof being opposite of each other and wherein a specific gap is formed between the opposite sides.
Figure 16B:
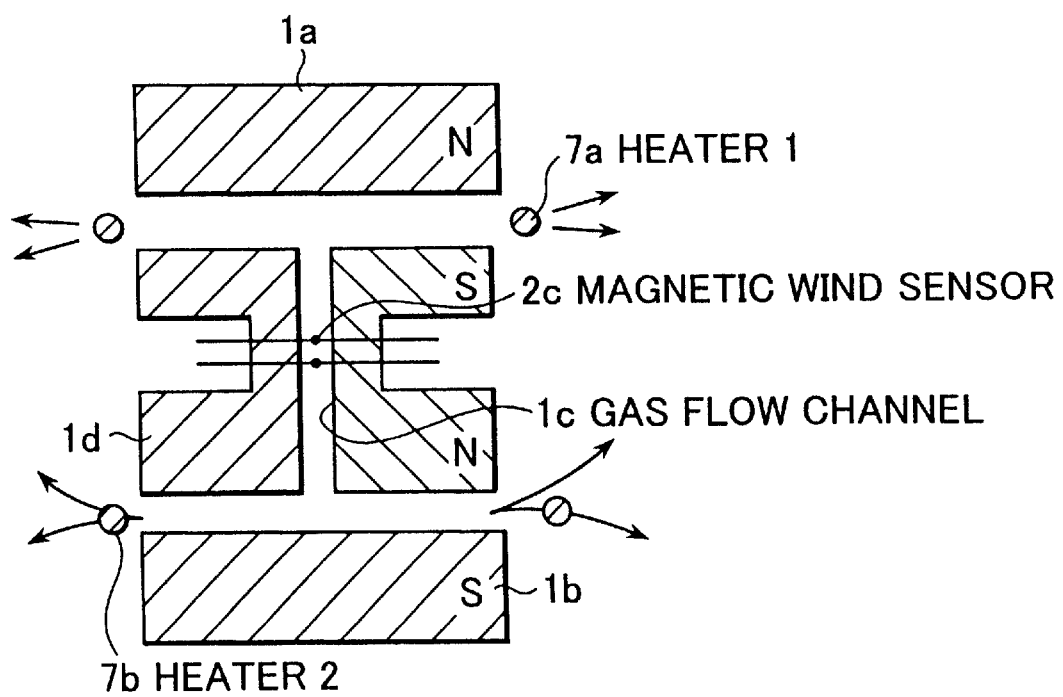

FIGS. 16(A) and 16(B) show another embodiment of the invention magnetic oxygen analyzer, comprising a bar shaped permanent magnet 1d wherein a through hole 1c is formed at nearly the midpoint thereof. An additional permanent magnet comprising poles 1a and 1b is placed on each side of the permanent magnet bar 1d with the polarities thereof being opposite to each other and specific gaps being formed respectively on each side of the perment magnet 1d. First heater 7a and second heater 7b are formed as continous wires, respectively, around the circumference of each magnetic field produced between opposite magnetic poles. Provided inside the through hole 1c or in the vicinity thereof are two magnetic wind sensors 2c. Also, the two magnetic wind sensors 2c are arranged so that one is disposed upstream of a magnetic wind flowing through the gas flow channel 1c (also called through hole) and the other downstream thereof, as shown in FIGS. 8(A) and 8(B). Also, the heaters are turned ON alternately at a frequency of, for example, 1 Hz by use of a heating circuit not shown. The resulting magnetic wind flows in the left direction of the arrow when the first heater 7a is kept ON or in the right direction of the arrow when the second heater 7b is turned ON. In this case, the outputs, i.e. resistance changes, of the two magnetic wind sensors largely differ from each other.

Note that if the first through fourth heaters 7a–7d are provided and switched ON/OFF alternately as shown, for example, in FIG. 15, noise may be produced in the detected magnetic wind because of thermal shock waves, i.e. by thermal convection that will occur during the ON/OFF sequence of the heaters.

FIG. 17 shows another embodiment, wherein noise in a detected signal, such as caused by thermal shock, is reduced. The embodiment comprises a flow channel 13 having a gas flow channel 13 with a smaller cross section as compared with that of the flow channel 14. Fixed onto both sides of flow channel 13 are flow channel 14 having gas flow channels with larger cross sections. Magnetic wind sensors 2c are disposed at nearly the midpoint of flow channel 13. Magnets, such as permanent magnets, 1a and 1b are disposed on the sides of flow channel 13.

A cover 15 is provided wherein a gas diffusion hole 17 is formed around the circumference thereof. Two covers 15 are mounted onto the ends of both flow channels 14 so as to cover the ends. The inner periphery of each flow channel 14 is sealed air tight with a O-ring 16. A heat 7 is stretched in a straight line across the inner surface of each cover 15 in a position opposite to nearly the midpoint of one end of the gas flow channel 13a. Although the flow channel 13 and flow channel 14 are of rectangular and circular shape, respectively, the bodies may be of any other suitable shape.

When the magnetic oxygen analyzer of FIG. 17 is disposed in a gas containing oxygen, the gas passes through the gas diffusion holes 17 to enter the flow channels 13 and 14. If the left and right side heaters 7, arranged to be within flow channel 14, are switched under this condition, thermal shock waves are produced at the moment of turning ON and OFF of the heaters. However, with the invention, such thermal shock waves are diffused such as by absorption, mainly at the flow channel 14 having a large cross section. Accordingly, it is possible, with the invention, to reduce the amount of shock waves that propagated to the gas flow channel 13 having a smaller cross section in which the magnetic wind sensors are installed.

FIG. 18 shows another embodiment of the magnetic oxygen analyzer of the invention, wherein thermal shock waves produced at the moment the heaters are turned ON and OFF are reflected by cover 15, thereby effectively preventing the waves from being propagated to the magnetic wind sensor side. FIG. 18 differs from FIG. 17 in that cover 15 is provided with a window 17 along heater 7. This analyzer embodiment can prevent thermal shock waves from being reflected by cover 15. Hence, it is possible to further reduce the effects of the thermal shock waves on the output of magnetic wind sensor 2c.

FIG. 19 shows another embodiment of the invention magnetic oxygen analyzer wherein the effects of thermal shock waves produced at the moment heaters 17 are turned ON and OFF are provided. The embodiment is characterized in that heater 7 is fixed in a position off the cross section of the gas flow channel 13a of the flow channel 13, which prevents thermal shock waves from directly entering the gas flow channel 13a. Hence, it is possible with the invention to reduce the effects of the waves on the output of the magnetic wind sensor 2c.

In the analyzer of FIG. 17, 18 or 19, there is slight possiblity that heat produced at heater 7 mounted on cover 15 may be transferred through flow channel 14 and channel 13 to the magnetic wind sensor 2c, thus adversely affecting the output of the sensor 2c. But, such possibility can be eliminated by fabricating both the flow channels 13 and 14 or either of the bodies using material of poor thermal conductivity, such as, for example, ceramic members.

In the foregoing embodiment, the magnetic oxygen analyzer used a metal resistance wire as the heat generator and a thermistor was used as the magnetic wind detector or sensor. Alternatively, a thermistor may be used as the heat generator, and a metal resistance wire, such as a platinum wire, may be used as the magnetic wind detector. Also, the heat generator and thermistor are mounted only one one side of the magnetic field. Alternatively, such heat generator and thermistor may be mounted on both sides of the magnetic field as long as the thermistor is disposed in such a position that it will not be affected by heat produced by the heat generator.

As discussed, the analyzer of the invention allows for easy control of the magnetic wind strength since a magnetic wind is produced by a heater and temperature detection is achieved by a thermistor.

Another advantage is that the heat generator and magnetic field are turned ON and OFF at fixed intervals to generate heat intermittently, and a band pass filter is used to allow the output of the magnetic wind sensor to pas through itself in synchronism with the interval of heat generation. Hence, it is possible to realize a magnetic oxygen analyzer that provides improved S/N ratio, is immune to ambient temperature, and eliminates the need for precise temperature control.

A further advantage is that non-magnetic material, to which no magnetic fields are applied and which has the same configuration as that of magnets, are arranged in the vicinity of the magnets, and arithmetic means are provided an output by subtracting the output from the non-magnetic materials from the output of the magnets, is incorporated. Hence, it is possible to realize a magnetic oxygen analyzer that is immune to the ambient temperature and to the mounted position of the analyzer, and one that eliminates need for precise temperature control.

A further advantage of the invention is that a flow channel comprising two continuous portions of large cross section and small cross section, is formed, wherein heat generator is placed in the large cross section portion and a magnetic wind sensor is disposed in the small cross section portion. Hence, it is possible to further reduce the effects of thermal shock waves on the output of the magnetic wind sensor.

Another advantage is that a flow channel of a large cross section is formed on both sides of a flow channel with a small cross section, heat generator means having the same heat generating capability are mounted on the large cross section flow channel, and the heat generator means are turned ON and OFF alternately. Hence, it is possible to cancel errors due to ambient temperature variations, and to further reduce the effects of thermal shock waves on the output of the magnetic wind sensor.

A yet further advantage is tht is is possible to reduce errors in the output of the magnetic wind sensor that occurs as a result of heat produced by a heater being transferred to the magnetic wind sensor side.

Figure 20:
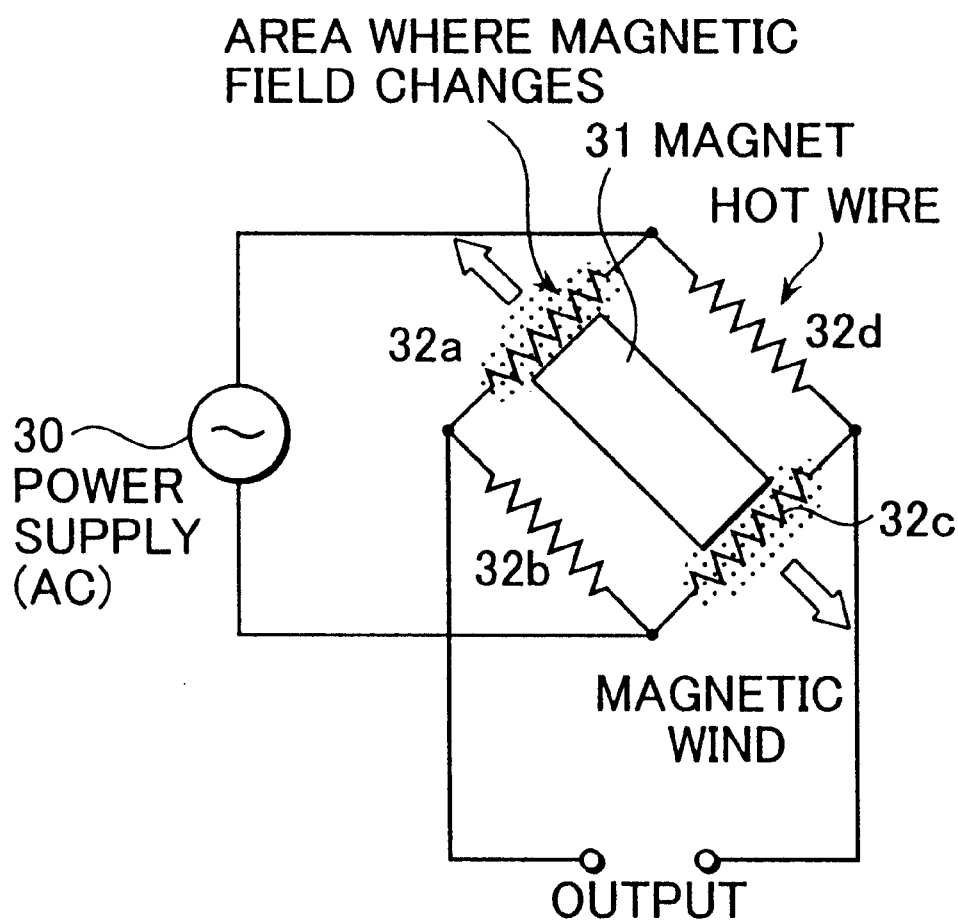
FIG. 20 is a circuit diagram depicting another illustrative embodiment of the invention, wherein AC voltage is used.

FIG. 20 shows the circuit diagram of the invention magnetic oxygen analyzer, wherein the source of power to the magnetic oxygen analyzer is an AC power supply. The circuit comprises a full bridge comprising four heat generator elements of the performance characteristics, e.g. hot wires made of tungsten, platinum or other material, the four components being used to form the bridge being of the same type and having the same characteristics of resistance change. A pair of oppositely positioned heat generators elements 32a and 32b are placed in an area with variable magnetic field intensity, i.e. are where the magnetic filed is changeable. Another pair of oppositely positioned hear generator elements 32b and 32d are placed in a position free from the effects of the magnetic field, i.e. in the magnetic wind.

The circuit comprises an AC power supply 30 having a frequency of, for example, 1 Hz. One of the AC power supply terminals is connected to a connection point between heat generator elements 32a and 32c. The other AC power supply terminal is connected to a connection point between heat generation elements 32b and 32d. The output terminals are connected to the connection points between heat generator elements 32a and 32e and between heat generator elements 32b and 32d.

Oxygen is gathered into a magnetic field by magnetization force, using the same operative principles as discussed above, when the analyzer is disposed in a mixed gas containing oxygen. Oxygen gas is thus gathered and is then heated by the heat generating elements arranged in an area with a variable magnetic field intensity. This results in a difference in magnetic susceptibility between oxygen gas having a reduced magnetic susceptibility due to heating and existing near the edges of the magnetic field and a non-heated oxygen gas having a reduced magnetic susceptibility and existing near the heat generator elements is driven away, thereby producing magnetid wind in the directions of the broad arrows pointing downward and upward.

All of the heat generator elements 32a–32d are turned ON at the same time because the power supply is of an AC type. However, since the pair of the oppositely positioned heat generator elements 32b and 32d, disposed in the area where the magnetic field is changed, causes a magnetic wind, and only the other pair of the oppositely positioned heat generator elements 32a and 32c of the full bridge is cooled by the magnetic wind.

As a result, a difference in temperature occurs between the pair of heat generator elements 32a and 32c and heat generator elements 32b and 32d, although all of these elements are turned ON at the same time. Accordingly, an AC output is produced from the bridge in the presence of oxygen.

Figure 21A:
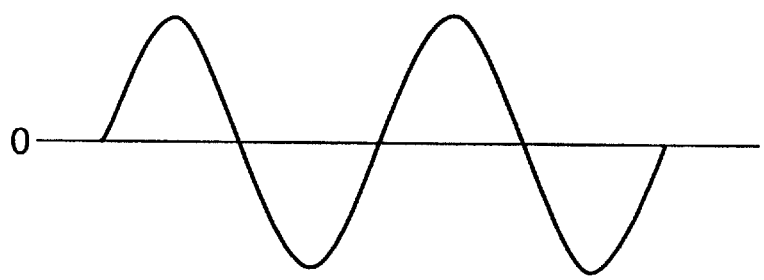
FIGS. 21(A)–21(C) are schematic views depicting output waveforms resulting from presence of absence of oxygen wherein AC voltage is used.
Figure 21B:
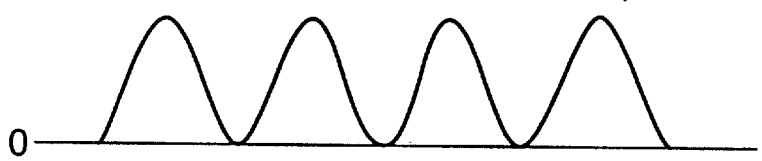
Figure 21C:

FIGS. 21(A), 21(B) and 21(C) show the voltage waveforms of the power supply and output waveforms provided in the presence and absence of oxygen. When the AC voltage shown in FIG. 21(A) is applied, the bridge output provides an output voltage waveform such as shown in FIG. 21(B) when oxygen is present. In the absence of oxygen, the bridge output provides a waveform such as shown in FIG. 21(C).

Figure 22:
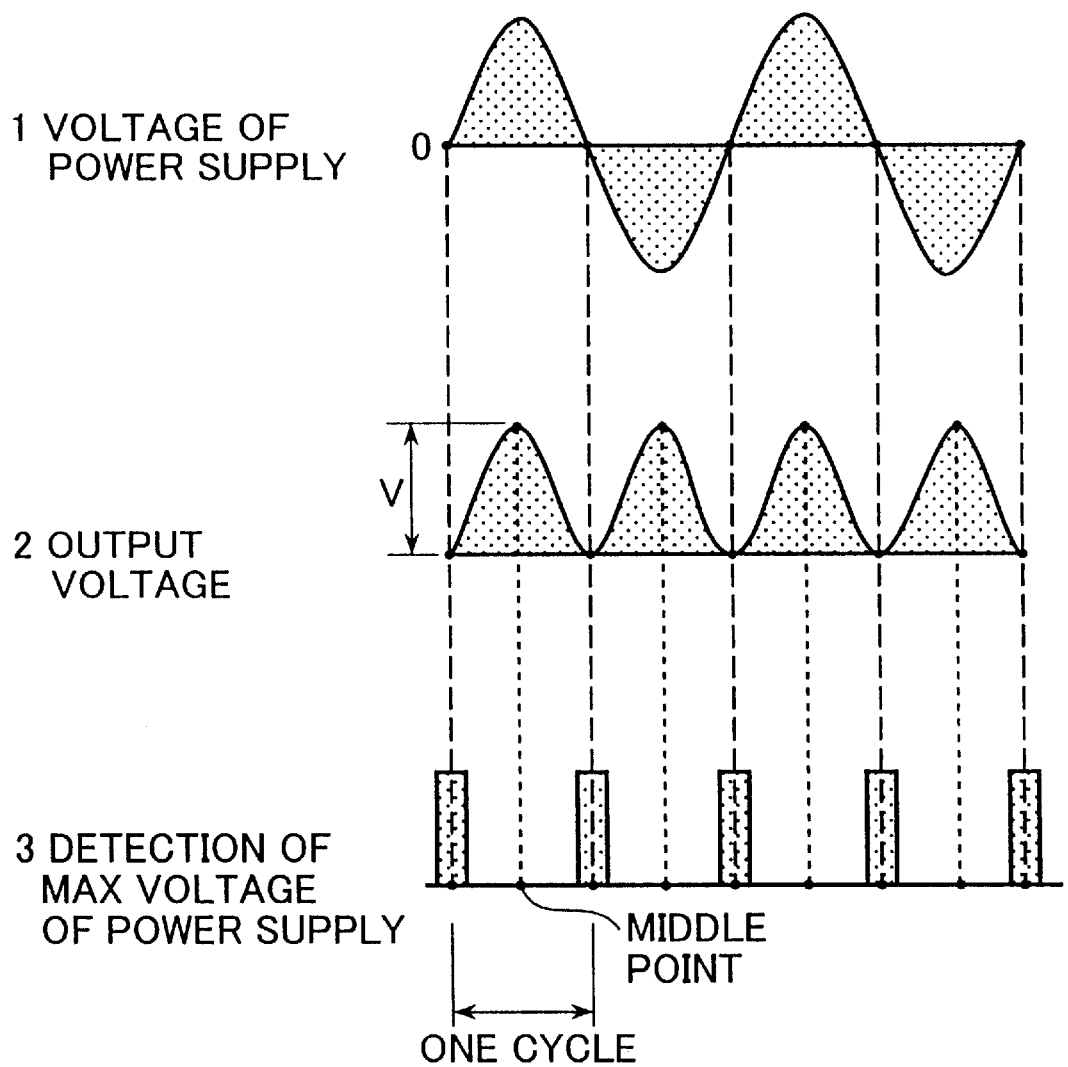
FIG. 22 is a chart depicting the relationship of a drive voltage waveform, an output voltage, and a voltage of a zero crossing detection signal.

FIGS. 22(A), 22(B) and 22(C) show the relationship of power supply voltage, an output voltage, and voltage of a zero crossing detector signal. From the relationship, the interval at which the power supply voltages passes through the zero crossing points is detected and the time corresponding to the middle point of one cycle, i.e. zero crossing interval, is determined also.

In the next step, the output voltages at the zero crossing point and middle point are determined and the difference between the output voltage (V–v) is evaluated. This difference varies with the strength of the magnetic wind. Hence, the oxygen concentration can be readily determined from the difference. With this approach it is possible to reduce the effects of any disturbance that may be caused by change in the mounting position, or by non-uniform distribution of ambient temperature and other factors which are irrelevant to the oxygen concentration.

FIGS. 23(a), 23(B) and 23(C) show the state of detector output when a zero point drift occurs. This drift causes a large output error in the case of a conventional DC current measurement method. In contrast, the invention method allows for detection of oxygen based signals alone, without being affected by the zero point drifts, since a difference between the output voltages at the zero crossing and the middle points (V–v) is detected.

Figure 24A:
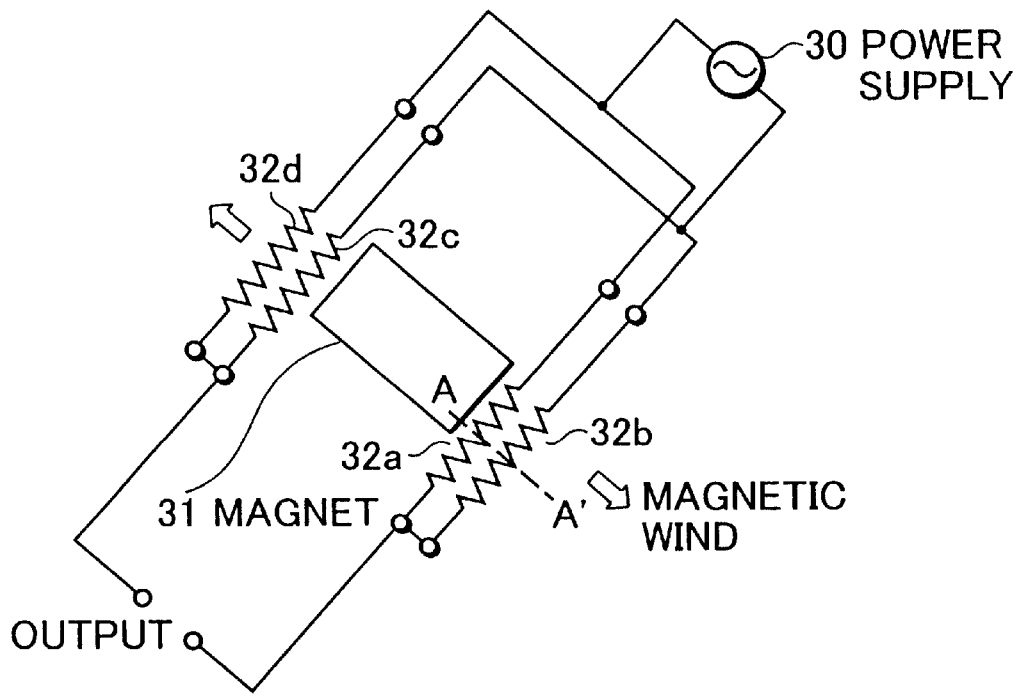
FIGS. 24(A) and 24(B) are schematic views depicting a further illustrative embodiment wherein AC voltage is used.
Figure 24B:
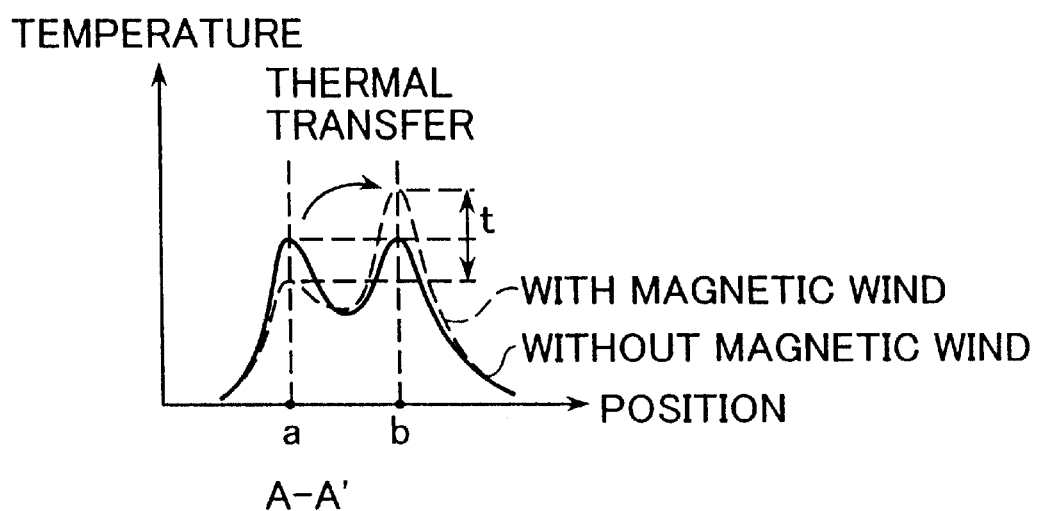

FIGS. 24(A), and 24(B) show another embodiment of the magnetic oxygen analyzer of the invention, wherein an AC power supply 30 is used as the source of power for the magnetic oxygen analyzer. The embodiment of FIG. 24(A) differs from that of FIG. 20 only in the position of one pair of heat generator elements. More specifically, as shown in FIG. 24(A), a pair of oppositely positioned heat generator elements 32a and 32c are disposed in an area with variable magnetic field intensity, i.e. in an area where the magnetic field is changed and oppositely disposed heat generator elements 32b and 32d of another pair are disposed in the vicinity of heat generator elements 32a and 32c, respectively, in a face to face manner.

FIG. 24(B) shows a temperature relationship between heat generator elements at a position A–A' when the magnetic oxygen analyzer of FIG. 24(A) is disposed in a gas containing oxygen and an AC voltage is supplied to the analyzer. The solid line curve represents the condition that oxygen does not exist and no magnetic wind is produced, whereas the dotted line curve represents the condition where a magnetic wind caused by the presence of oxygen is present. More specifically, the dotted line curve indicates that the heat generator element 32a is cooled by the magnetic wind and the heat generator element 32b disposed downstream of the magnetic wind becomes hotter as the element is affected by heat from heat generator element 32a, thereby increasing the temperature difference, i.e. the resistance change. Hence, the level of the bridge output becomes higher, as compared with that of the embodiment shown in FIG. 20, thus improving the S/N ratio of the magnetic oxygen analyzer.

The above embodiment uses tungsten or platinum as the material for the heat generator elements. A problem may arise with the analyzer is that the heat generator elements may be relatively expensive when economic considerations are important. Another problem is that it is difficult to fabricate heat generator elements having the same level of accuracy and to match temperature condidtions of four heat generator elements to one another.

Figure 25:
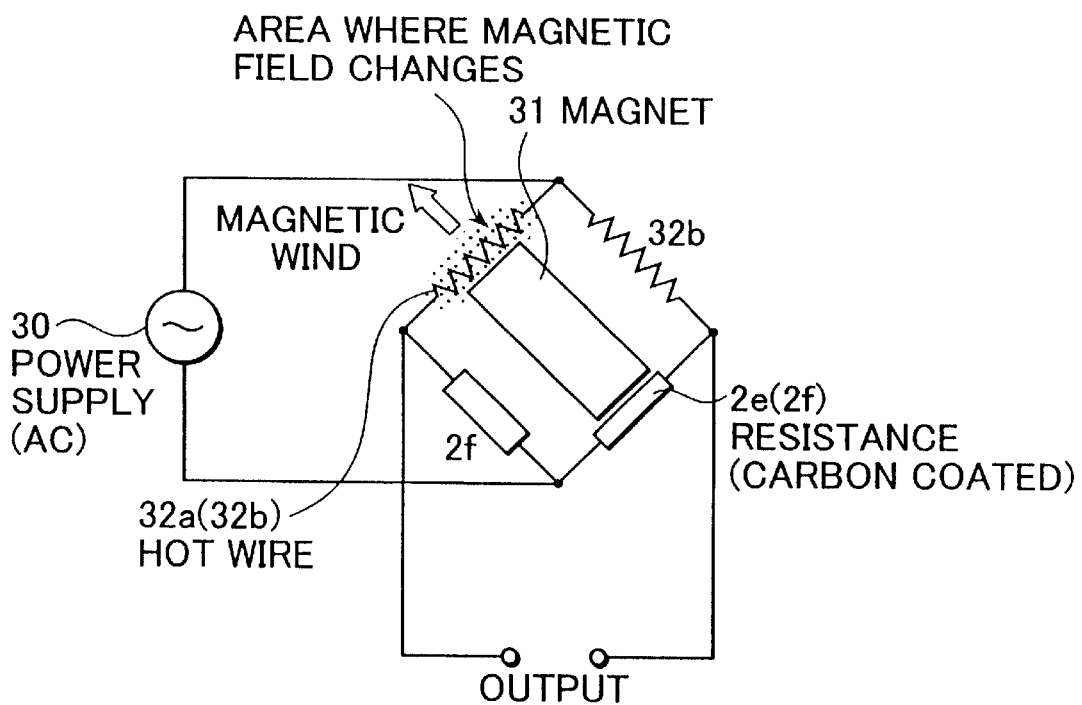
FIG. 25 is a schematic view depicting another illustrative embodiment wherein AC voltage is used.

FIG. 25 shows another embodiment of a magnetic oxygen analyzer of the invention, wherein two oppositely positioned heat generators made of, for example, carbon-film resistors having the same level of accuracy are used to form a half bridge. Among the four electronic, components forming the bridge, two are elements having the same characteristic of resistance change by heating and another two are pure resistors. In addition, only the heat generator element 32a is disposed in the area where the magnetic field is changed. Also, in this case, the waveforms of the power supply voltage, output voltage and zero crossing detection signal voltage are the same as those shown in FIGS. 22(A)–22(C). Hence, it is possible to detect oxygen based signals, without being affected by zero point drifts, by detecting a difference between each peak of the zero crossing detection signal voltage and each peak of the output voltage produced at every other peak of the zero crossing signal and in synchronism with each middle point thereof.

The magnetic oxygen analyzer of the embodiment has half the sensitivity of an analyzer using four heat generator elements. On the other hand, it becomes possible to reduce the cost of the analyzer as a whole, since carbon coated resistances, which are inexpensive as compared with heat generator elements, are used as components in the bridge of this case. Another advantage is that only two heat generator elements of the same accuracy need to be fabricated and the temperature conditions thereof matched to each other.

Although a sine wave is used as the voltage waveform of the power supply in this embodiment, a rectangular wave can also be used.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. A magnetic oxygen analyzer comprising:
  generator means for producing magnetic fields from oppositely arranged magnetic poles;
  heat generator means for producing heat to cause magnetic wind, said heat generator means being disposed in an area of a non-uniform magnetic field whereat intensity of magnetic field is caused to vary; and magnetic wind sensor means for detecting said magnetic wind, said magnetic wind sensor means being disposed in a position whereat said magnetic wind sensor means is not affected by heat produced by said heat generator means;

wherein an electrical resistance change in said magnetic wind sensor means is detected as oxygen concentration in a mixed gas by detecting relative strength of said magnetic wind blown onto said genetic wind sensor means.

2. The analyzer of claim 1, wherein said generator means comprises a plurality of pairs of means for producing magnetic fields; and wherein said heat generator means comprises a plurality of heat generating means having the same construction as that of said generator means; and wherein said plurality of heat generating means are disposed to sandwich said magnetic wind sensor means and thereby increase volume of said magnetic wind.

3. The analyzer of claim 1, wherein said generator means comprises a pair of magnetic poles and wherein said heat generator means comprises heating means formed around a circumference of said pair of magnetic poles, one of said magnetic poles having a through hole therein leading to a space one side of which is enclosed by said heating means, and wherein said magnetic wind sensor means are disposed inside or in vicinity of said through hole.

4. The analyzer of claim 1, wherein said heat generator means comprises means for turning ON/OFF said generator means at fixed intervals to generate heat intermittently, and further comprising a band pass filter for filtering an electrical signal, said electrical signal corresponding to a change in electrical characteristics of said heat generator means caused by generation of said magnetic wind, in synchronism with interval of heat generation by said heat generator means.

5. The analyzer of claim 1, wherein said heat generator means comprises means for turning ON and OFF said heat generator means at fixed intervals to generate heat intermittently, and further comprising a band pass filter for filtering an electrical signal, said electrical signal varying according to a resistance change in said magnetic wind sensor means in synchronism with interval of heat generation by said heat generator means.

6. The analyzer of claim 1, wherein said generator means comprises means for turning ON and OFF said magnetic field at fixed intervals, and further comprising a band pass filter for filtering an electric signal, said electrical signal varying according to resistance change in said magnetic wind sensor means, in synchronism with ON/OFF interval of said magnetic field.

7. The analyzer of claim 1, wherein said heat generator means and said magnetic wind sensor means are made of either metal resistance wire or sintered metal oxide material.

8. A magnetic oxygen analyzer comprising:

magnetic field generator means for producing a magnetic field from oppositely arranged magnetic poles;

a metal resistance wire or sintered metal oxide material disposed in an area whereat intensity of said magnetic field in varied and for producing heat to produce magnetic wind;

a plurality of magnets for detecting an electrical resistance change in said metal resistance wire or sintered metal oxide material caused by said magnetic wind relative to said magnetic field and to oxygen concentration of a mixed gas containing oxygen;

a plurality of dummy magnets having similar construction as that of said plurality of magnets and disposed in an area where no magnetic field is applied, said plurality of dummy magnets being arranged close to said plurality of magnets; and arithmetic means for providing an output signal by subtracting an output from said plurality of dummy magnets from an output from said plurality of magnets.

9. The analyzer of claim 8, wherein said metal resistance wire or sintered metal oxide material serve as a heat generator.

10. A magnetic oxygen analyzer comprising:

means for generating a magnetic field from oppositely arranged magnetic poles;

a pair of heat generator means for producing heat to provide magnetic wind, said heat generator means being disposed in an area of non-uniform magnetic field whereat intensity of said magnetic field is varied and wherein said pair of heat generator means are turned ON and OFF alternately; and a pair of magnetic wind sensors disposed in a position not affected by heat from said heat generator means and disposed to be perpendicular to direction of magnetic wind flow and to be close to each other;

wherein an electrical resistance change in said pair of magnetic wind sensors caused by relative strength of magnetic wind is detected as oxygen concentration of a mixed gas when magnetic wind is blown onto said pair of magnetic wind sensors.

11. The analyzer of claim 10, wherein said means for generating a magnetic field comprises a pair of magnetic field generating means; and wherein said pair of heat generator means have the same construction as said pair of magnetic field generating means; and wherein said pair of heat generator means are disposed to sandwich said pair of magnetic wind sensors, thereby to increase volumetric flow rate of said magnetic wind.

12. The analyzer of claim 10, wherein said heat generator means and said magnetic wind sensor means comprise metal resistance wire or sintered metal oxide material.

13. The analyzer of claim 10, further comprising means for providing an output value by subtracting output of said magnetic wind sensor disposed downstream of said magnetic wind from output of said magnetic sensor disposed upstream of said magnetic wind.

14. A magnetic oxygen analyzer comprising:

magnetic field generation means for generating magnetic fields from oppositely arranged magnetic poles;

a full bridge comprising four heat generating elements of generally the same type which produce heat and an electrical resistance thereof being changed when turned ON; and an AC power supply;

wherein one pair of oppositely positioned said heat generating elements is oppositely arranged in an area wherein intensity of magnetic field is variable so as to sandwich a uniform part of said magnetic field, and wherein another pair of oppositely positioned said heat generating elements are disposed in a position which is free from effects of said magnetic field; and wherein said AC power supply supplies AC power across said full bridge.

15. A magnetic oxygen analyzer comprising:

magnetic field generating means for producing magnetic fields from oppositely disposed magnetic poles;

a full bridge comprising four heat generating elements of generally the same type which produce heat and whose set of electrical resistances change when turned ON; and AC power supply;

wherein one pair of oppositely positioned said heat generating elements are oppositely disposed in an area with variable magnetic field intensity so as to sandwich a uniform part of said magnetic fields; wherein another pair of oppositely positioned said heat generating elements are disposed in vicinity of said one pair of heat generating elements; and wherein said AC power supply supplies AC voltage across said full bridge.

16. The analyzer of claim 14, wherein said heat generating means comprises tungsten or platinum.

17. The analyzer of claim 15, wherein said heat generating means comprises tungsten or platinum.

18. A magnetic oxygen analyzer comprising:

magnetic field generating means for providing magnetic field from oppositely arranged magnetic poles;

a half bridge comprising a pair of heat generating elements of generally the same type which produce heat and whose set of electrical resistances change when turned ON; and an AC power supply;

wherein one of said pair of heat generating elements is disposed in an area where magnetic field intensity is varied, and the other of said pair of heating elements is disposed to be in an area free of effects of said magnetic field.

* * * * *